United States Patent
Jackson et al.

(10) Patent No.: US 10,161,929 B2
(45) Date of Patent: Dec. 25, 2018

(54) THERANOSTICS PLATFORM AND METHODS OF USE

(71) Applicant: Sanford Burnham Prebys Medical Discovery Institute, La Jolla, CA (US)

(72) Inventors: Michael Jackson, La Jolla, CA (US); Anne Bang, La Jolla, CA (US)

(73) Assignee: Sanford Burnham Prebys Medical Discovery, La Jolla, CA (US)

( * ) Notice: Subject to any disclaimer, the term of this patent is extended or adjusted under 35 U.S.C. 154(b) by 429 days.

(21) Appl. No.: 14/378,283

(22) PCT Filed: Feb. 15, 2013

(86) PCT No.: PCT/US2013/026448
§ 371 (c)(1),
(2) Date: Aug. 12, 2014

(87) PCT Pub. No.: WO2013/123403
PCT Pub. Date: Aug. 22, 2013

(65) Prior Publication Data
US 2015/0018240 A1  Jan. 15, 2015

Related U.S. Application Data

(60) Provisional application No. 61/599,327, filed on Feb. 15, 2012, provisional application No. 61/599,319, filed on Feb. 15, 2012.

(51) Int. Cl.
*G01N 33/50* (2006.01)

(52) U.S. Cl.
CPC ....... *G01N 33/5026* (2013.01); *G01N 33/502* (2013.01); *G01N 2333/78* (2013.01); *G01N 2500/02* (2013.01); *G01N 2500/10* (2013.01); *G01N 2800/2878* (2013.01)

(58) Field of Classification Search
CPC .......................... G01N 33/5026; G01N 33/502
USPC .......................................................... 506/9
See application file for complete search history.

(56) References Cited

U.S. PATENT DOCUMENTS

| | | | | | |
|---|---|---|---|---|---|
| 5,780,244 | A | * | 7/1998 | Engvall | C12Q 1/6883 435/7.1 |
| 2002/0076689 | A1 | * | 6/2002 | Farb | G01N 33/48728 435/4 |
| 2003/0096309 | A1 | * | 5/2003 | Borisy | C12Q 1/6897 435/7.1 |
| 2005/0239201 | A1 | * | 10/2005 | Mollard | C12N 5/0683 435/354 |
| 2008/0208784 | A1 | * | 8/2008 | Hill | G06F 19/12 706/46 |
| 2012/0041279 | A1 | * | 2/2012 | Freeman | A61B 5/0205 600/301 |
| 2012/0220022 | A1 | * | 8/2012 | Ehrlich | G01N 15/14 435/286.2 |
| 2013/0052160 | A1 | * | 2/2013 | Zitvogel | C12Q 1/6886 424/85.2 |
| 2013/0203764 | A1 | * | 8/2013 | Djamgoz | A61K 31/00 514/252.12 |

FOREIGN PATENT DOCUMENTS

WO   WO2013/123403   8/2013

OTHER PUBLICATIONS

Meirelles et al., Journal of Cell Science, 119, 2006, pp. 2204-2213.*
Chun et al., Int. J. Biol. Sci., 2010, 6, pp. 796-805.*
Takahashi et al., Cell, 126, Aug. 25, 2006, pp. 663-676.*
Hedlund et al., Stem Cells, Jun. 2008, 26(6), pp. 1526-1536.*
Chapter 4: Discovery Research for Rare Diseases and Orphan Product Development. Rare Diseases and Orphan Products: Accelerating Research and Development. Institute of Medicine of the National Academies. 2010. pp. 111-146. Available at http://www.ncbi.nlm.nih.gov/books/NBK56191/.
Chong et al. New Uses for Old Drugs. Nature. 2007. 448(7154):645-656.
Lee et al. Modelling Familial Dysautonomia in Human Induced Pluripotent Stem Cells, Philosophical Transactions of the Royal Society B: Biological Sciences. 2011. 366:2286-2296.
PCT/US2013/026448 International Preliminary Report on Patentability dated Aug. 19, 2014.
PCT/US2013/026448 International Search Report dated May 14, 2013.

* cited by examiner

*Primary Examiner* — Karla A Dines
(74) *Attorney, Agent, or Firm* — Wilson Sonsini Goodrich & Rosati

(57) ABSTRACT

Theranostics platforms for identifying drugs and nutraceuticals for treatment of rare disease are described. The platforms comprise (a) a cell-phenotype image-enhancing instrument; (b) a drug/nutraceutical library; and (c) a computer-implemented system for analyzing a response of an optically-visible rare-disease cell phenotype to a drug or nutraceutical from the drug/nutraceutical library.

18 Claims, 10 Drawing Sheets

POMT1 : Protein-O-mannosyltransferase1

THERANOSTICS PLATFORM AND METHODS OF USE

CROSS-REFERENCE TO RELATED APPLICATIONS

This application is the National Phase entry of International Application No. PCT/US2013/026448, filed Feb. 15, 2013, which claims the benefit of priority of U.S. Provisional Application No. 61/599,319 filed on Feb. 15, 2012, and U.S. Provisional Application No. 61/599,327 filed on Feb. 15, 2012, the contents of each are incorporated by reference herein in their entirety.

SUMMARY OF INVENTION

Disclosed herein, in certain embodiments, are rare disease theranostics platforms, comprising: (a) a cell-phenotype image-enhancing instrument; (b) a drug/nutraceutical library; and (c) a computer-implemented system for analyzing responses of an optically-visible rare-disease cell-phenotype of a cell to a drug or nutraceutical from the drug/nutraceutical library. In some embodiments, the optically-visible rare-disease cell-phenotype is associated with a rare disease. In some embodiments, the cell-phenotype image-enhancing instrument detects the response of the optically-visible rare-disease cell-phenotype to a drug or nutraceutical from the drug/nutraceutical library. In some embodiments, the cell-phenotype image-enhancing instrument is a microscope. In some embodiments, the microscope comprises: (a) a detector for imaging the optically-visible rare-disease phenotype; (b) magnification optics having sufficient magnifying power to visualize one cell in a plurality of cells; and (c) an available electronic memory for storing an image of a cell. In some embodiments, the cell with the optically-visible rare-disease cell phenotype was differentiated from a stem cell obtained from a subject that has symptoms of the rare disease, has limited symptoms of the rare disease or is asymptomatic. In some embodiments, the drug/nutraceutical library comprises commercially available nutraceuticals, or approved therapeutic agents. In some embodiments, the drug/nutraceutical library comprises at least 500 commercially available nutraceuticals, approved therapeutic agents, or combinations thereof. In some embodiments, the computer-implemented system comprises an algorithm that determines degrees of response of the optically-visible rare-disease phenotype to a drug or nutraceutical in the drug/nutraceutical library. In some embodiments, the computer-implemented system correlates the response of the optically-visible rare-disease phenotype to a drug or nutraceutical in the drug/nutraceutical library with the effect of the drug or nutraceutical on at least one symptom of the rare disease in vivo. In some embodiments, the rare disease theranostic platforms further comprise an assay for a biomarker that correlates with the rare-disease phenotype. In some embodiments, the biomarker is present in blood, plasma, or cell culture medium. In some embodiments, the optically-visible rare-disease phenotype comprises an optically-visible tag. In some embodiments, the optically-visible tag is a fluorescent tag. In some embodiments, the optically-visible rare-disease phenotype is selected from cell morphology, nuclear morphology or morphology of any cytosolic organelle. In some embodiments, the cell with the optically-visible rare-disease cell phenotype is a myocyte. In some embodiments, the computer-implemented system comprises an algorithm that correlates the rare-disease phenotype with the severity of the rare-disease in the subject. In some embodiments, the optically-visible rare-disease cell-phenotype is abnormal laminin binding, or abnormal lamin A/C or lamin B binding. In some embodiments, the rare disease is laminopathy, Fukuyama congenital muscular dystrophy(FCMD), congenital muscular dystrophy unrelated to FCMD, Duchenne muscular dystrophy, Becker's muscular dystrophy, distal muscular dystrophy, Emery-Dreifuss muscular dystrophy, facioscapulohumeral muscular dystrophy, Limb-girdle muscular dystrophy, myotonic muscular dystrophy, or oculopharyngeal muscular dystrophy. In some embodiments, the rare disease is Duchenne muscular dystrophy. In some embodiments, the rare disease is laminopathy. In some embodiments, the rare disease is junctional epidermolysis bullosa or nephrotic syndrome.

Disclosed herein, in certain embodiments, are methods of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) obtaining a magnified image of the plurality of cells following contact with the drug or nutraceutical from the drug/nutraceutical library; and (c) using a computer-implemented algorithm to analyze the magnified images to determine the response of the plurality of cells to the drug or nutraceutical from the drug/nutraceutical library; wherein a drug or nutraceutical that normalizes or partially normalizes the optically-visible rare-disease cell phenotype is identified as a candidate for normalizing, or partially normalizing the optically-visible rare-disease cell phenotype in a subject in need thereof. In some embodiments, the optically-visible rare-disease cell-phenotype is associated with a rare disease. In some embodiments, the subject in need thereof has symptoms of the rare disease, has limited symptoms of the rare disease or is asymptomatic. In some embodiments, the optically visible rare-disease cell phenotype is cell morphology, nuclear morphology and morphology of any cytosolic organelle. In some embodiments, the optically visible rare-disease cell phenotype is abnormal laminin binding, or abnormal lamin A/C or lamin B binding. In some embodiments, the methods further comprise using a phenotype image-enhancing instrument to obtain the magnified image of the plurality of cells. In some embodiments, the phenotype image-enhancing instrument is a microscope. In some embodiments, the methods further comprise assaying for a biomarker that correlates with the rare-disease phenotype. In some embodiments, the biomarker is present in blood, plasma, or cell culture medium. In some embodiments, the methods further comprise contacting the plurality of cells with an optically-visible tag to produce the optically-visible rare-disease cell phenotype. In some embodiments, the optically-visible tag is a fluorescent tag. In some embodiments, the methods further comprise using a computer-implemented algorithm to correlate the optically-visible rare-disease phenotype with the severity of the optically-visible rare-disease phenotype in vivo. In some embodiments, the rare disease is laminopathy, Fukuyama congenital muscular dystrophy(FCMD), congenital muscular dystrophy unrelated to FCMD, Duchenne muscular dystrophy, Becker's muscular dystrophy, distal muscular dystrophy, Emery-Dreifuss muscular dystrophy, facioscapulohumeral muscular dystrophy, Limb-girdle muscular dystrophy, myotonic muscular dystrophy, or oculopharyngeal muscular dystrophy. In some embodiments, the rare disease is Duchenne muscular dystrophy. In some embodiments, the rare disease is laminopathy. In some embodiments, the rare disease is junctional epidermolysis bullosa or nephrotic syndrome.

Disclosed herein, in certain embodiments, are methods of identifying a drug or nutraceutical candidate for normalizing, or partially normalizing, an optically-visible rare-disease phenotype in a subject in need thereof, comprising (a) using a computer-implemented algorithm to analyze a magnified image of a plurality of cells with the optically-visible rare-disease phenotype that have been contacted with a drug or nutraceutical from a drug/nutraceutical library to determine the response of the plurality of cells to the drug or nutraceutical; and (b) identifying a drug or nutraceutical that normalizes or partially normalizes the optically-visible rare-disease cell phenotype as a candidate for normalizing, or partially normalizing, an optically-visible rare-disease cell phenotype in a subject in need thereof. In some embodiments, the optically-visible rare-disease cell-phenotype is associated with a rare disease. In some embodiments, the subject in need thereof has symptoms of the rare disease, has limited symptoms of the rare disease or is asymptomatic. In some embodiments, the optically visible rare-disease cell phenotype is cell morphology, nuclear morphology and morphology of any cytosolic organelle. In some embodiments, the optically visible rare-disease cell phenotype is abnormal laminin binding, or abnormal lamin A/C or lamin B binding. In some embodiments, the methods further comprise using a phenotype image-enhancing instrument to obtain the magnified image of the plurality of cells. In some embodiments, the phenotype image-enhancing instrument is a microscope. In some embodiments, the methods further comprise assaying for a biomarker that correlates with the rare-disease phenotype. In some embodiments, the biomarker is present in blood, plasma, or cell culture medium. In some embodiments, the methods further comprise contacting the plurality of cells with an optically-visible tag to produce the optically-visible rare-disease cell phenotype. In some embodiments, the optically-visible tag is a fluorescent tag. In some embodiments, the methods further comprise using a computer-implemented algorithm to correlate the optically-visible rare-disease phenotype with the severity of the optically-visible rare-disease phenotype in vivo. In some embodiments, the rare disease is laminopathy, Fukuyama congenital muscular dystrophy(FCMD), congenital muscular dystrophy unrelated to FCMD, Duchenne muscular dystrophy, Becker's muscular dystrophy, distal muscular dystrophy, Emery-Dreifuss muscular dystrophy, facioscapulohumeral muscular dystrophy, Limb-girdle muscular dystrophy, myotonic muscular dystrophy, or oculopharyngeal muscular dystrophy. In some embodiments, the rare disease is Duchenne muscular dystrophy. In some embodiments, the rare disease is laminopathy. In some embodiments, the rare disease is junctional epidermolysis bullosa or nephrotic syndrome.

Disclosed herein, in certain embodiments, are rare disease theranostics platforms, comprising: (a) a cell-phenotype image-enhancing instrument; (b) a drug/nutraceutical library; and (c) a computer-implemented system for analyzing a response of an optically-visible rare-disease cell phenotype to a drug or nutraceutical from the drug/nutraceutical library. In some embodiments, the response of the optically-visible rare-disease cell phenotype to a drug or nutraceutical from the drug/nutraceutical library is detected by the cell-phenotype image-enhancing instrument. In some embodiments, the cell-phenotype image-enhancing instrument is a microscope. In some embodiments, the microscope comprises: (a) a detector for imaging the optically-visible rare-disease cell phenotype; (b) magnification optics having sufficient magnifying power to visualize one cell in a plurality of cells; and (c) an available electronic memory for storing an image of a cell. In some embodiments, the drug/nutraceutical library comprises commercially available nutraceuticals, or approved therapeutic agents. In some embodiments, the drug/nutraceutical library comprises at least 500 commercially available nutraceuticals, approved therapeutic agents, or combinations thereof. In some embodiments, the computer-implemented system comprises an algorithm that determines degrees of response of the optically-visible rare-disease cell phenotype to a drug or nutraceutical in the drug/nutraceutical library. In some embodiments, the rare-disease cell phenotype correlates with the severity of the rare-disease in the subject. In some embodiments, the response of the optically-visible rare-disease cell phenotype to a drug or nutraceutical in the drug/nutraceutical library correlates with the effect of the drug or nutraceutical on at least one symptom of the rare disease in vivo. In some embodiments, the rare-disease phenotype in a subject has gradations of severity, from undetectable to severely debilitating. In some embodiments, the system further comprises assaying a biomarker that correlates with the rare-disease cell phenotype. In some embodiments, the biomarker is present blood, plasma, or cell culture medium. In some embodiments, the optically-visible rare-disease cell phenotype comprises an optically-visible tag. In some embodiments, the optically-visible tag is a fluorescent tag. In some embodiments, the optically-visible rare-disease cell phenotype is selected from cell morphology, nuclear morphology or morphology of any cytosolic organelle. In some embodiments, the platform enables high-throughput screening of the drug/nutraceutical library. In some embodiments, the platform identifies at least one drug or nutraceutical from the library that normalizes or partially normalizes the optically-visible rare-disease cell phenotype. In some embodiments, the system further comprises differentiating a stem cell obtained from the subject into a cell with the optically-visible rare-disease cell phenotype.

Disclosed herein, in certain embodiments, are methods of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) obtaining a magnified image of the plurality of cells following contact with the drug or nutraceutical from the drug/nutraceutical library; and (c) analyzing the magnified images to determine the response of the plurality of cells to the drug or nutraceutical from the drug/nutraceutical library. In some embodiments, a drug or nutraceutical that normalizes or partially normalizes the optically-visible rare-disease cell phenotype is identified as a candidate for normalizing, or partially normalizing the optically-visible rare-disease cell phenotype in a subject in need thereof. In some embodiments, a computer-implemented algorithm analyzes the magnified images to determine the response of the plurality of cells to the drug or nutraceutical from the drug/nutraceutical library. In some embodiments, the optically-visible rare-disease cell phenotype correlates with the severity of the optically-visible rare-disease phenotype in vivo. In some embodiments, the method further comprises contacting the plurality of cells with an optically-visible tag to produce the optically-visible rare-disease cell phenotype. In some embodiments, the optically-visible tag is a fluorescent tag. In some embodiments, the optically visible rare-disease cell phenotype is selected from cell morphology, nuclear morphology and morphology of a cytosolic organelle.

Disclosed herein, in certain embodiments, are methods of treating at least one rare-disease cell phenotype in a subject in need thereof, comprising administering to the subject the drug or nutraceutical candidate identified by any method disclosed herein.

Disclosed herein, in certain embodiments, are Rare Disease Specific Drug Libraries obtained by any of the methods or platforms disclosed herein.

Disclosed herein, in certain embodiments, are theranostics platforms for a disease or condition associated with abnormal laminin binding, comprising: (a) a cell-phenotype image-enhancing instrument; (b) a drug/nutraceutical library; and (c) a computer-implemented system for analyzing a response of abnormal laminin binding cell-phenotype to a drug or nutraceutical from the drug/nutraceutical library. In some embodiments, the responses of the abnormal laminin binding cell-phenotype to a drug or nutraceutical from the drug/nutraceutical library are detected by the cell-phenotype image-enhancing instrument. In some embodiments, the cell-phenotype image-enhancing instrument is a microscope. In some embodiments, the microscope comprises: (a) a detector for imaging the abnormal laminin binding cell-phenotype; (b) magnification optics having sufficient magnifying power to visualize one cell in a plurality of cells; and (c) an available electronic memory for storing an image of a cell. In some embodiments, the drug/nutraceutical library comprises commercially available nutraceuticals, or approved therapeutic agents. In some embodiments, the drug/nutraceutical library comprises at least 500 commercially available nutraceuticals, approved therapeutic agents, or combinations thereof. In some embodiments, the computer-implemented system comprises an algorithm that determines degrees of response of the abnormal laminin binding cell-phenotype to a drug or nutraceutical in the drug/nutraceutical library. In some embodiments, the cell phenotype correlates with the severity of the disease or condition associated with abnormal laminin binding in the subject. In some embodiments, the response of the abnormal laminin binding cell-phenotype to a drug or nutraceutical in the drug/nutraceutical library correlates with the effect of the drug or nutraceutical on at least one symptom of the disease or condition associated with abnormal laminin binding in vivo. In some embodiments, the abnormal laminin binding cell-phenotype in a subject has gradations of severity, from undetectable to severely debilitating. In some embodiments, the platforms further comprise assaying a biomarker that correlates with the abnormal laminin binding cell-phenotype. In some embodiments, the biomarker is present in blood, plasma, or cell culture medium. In some embodiments, the abnormal laminin binding cell-phenotype comprises an optically-visible tag. In some embodiments, the optically-visible tag is a fluorescent tag. In some embodiments, the platform enables high-throughput screening of the drug/nutraceutical library. In some embodiments, the platform identifies at least one drug or nutraceutical from the library that normalizes or partially normalizes the abnormal laminin binding cell-phenotype. In some embodiments, the platforms further comprise differentiating a stem cell obtained from the subject into a cell with the abnormal laminin binding cell-phenotype. In some embodiments, the disease or condition associated with abnormal laminin binding is Fukuyama congenital muscular dystrophy(FCMD), congenital muscular dystrophy unrelated to FCMD, Duchenne muscular dystrophy, Becker's muscular dystrophy, distal muscular dystrophy, Emery-Dreifuss muscular dystrophy, facioscapulohumeral muscular dystrophy, Limb-girdle muscular dystrophy, myotonic muscular dystrophy, or oculopharyngeal muscular dystrophy. In some embodiments, the disease or condition associated with abnormal laminin binding is Duchenne muscular dystrophy. In some embodiments, the disease or condition associated with abnormal laminin binding is junctional epidermolysis bullosa or nephrotic syndrome.

Disclosed herein, in certain embodiments, are methods of identifying a drug or nutraceutical candidate for normalizing, or partially normalizing, an abnormal laminin binding cell-phenotype in a subject in need thereof, comprising the steps of: (a) contacting a plurality of cells with the abnormal laminin binding cell-phenotype with a drug or nutraceutical from a drug/nutraceutical library; (b) obtaining a magnified image of the plurality of cells following contact with the drug or nutraceutical from the drug/nutraceutical library; and (c) analyzing the magnified images to determine the response of the plurality of cells to the drug or nutraceutical from the drug/nutraceutical library. In some embodiments, a drug or nutraceutical that normalizes or partially normalizes the abnormal laminin binding cell-phenotype is identified as a candidate for normalizing, or partially normalizing the abnormal laminin binding cell-phenotype in a subject in need thereof. In some embodiments, a computer-implemented algorithm analyzes the magnified images to determine the response of the plurality of cells to the drug or nutraceutical from the drug/nutraceutical library. In some embodiments, the abnormal laminin binding cell-phenotype correlates with the severity of the disease or condition associated with abnormal laminin binding in vivo. In some embodiments, the methods further comprise contacting the plurality of cells with an optically-visible tag to produce the abnormal laminin binding cell-phenotype. In some embodiments, the optically-visible tag is a fluorescent tag.

Disclosed herein, in certain embodiments, are methods of treating disease or condition associated with abnormal laminin binding cell-phenotype in a subject in need thereof, comprising administering to the subject the drug or nutraceutical candidate identified by the a method described herein, wherein the disease or condition associated with abnormal laminin binding is Fukuyama congenital muscular dystrophy(FCMD), congenital muscular dystrophy unrelated to FCMD, Duchenne muscular dystrophy, Becker's muscular dystrophy, distal muscular dystrophy, Emery-Dreifuss muscular dystrophy, facioscapulohumeral muscular dystrophy, Limb-girdle muscular dystrophy, myotonic muscular dystrophy, or oculopharyngeal muscular dystrophy. In some embodiments, the disease or condition associated with abnormal laminin binding is Duchenne muscular dystrophy. In some embodiments, the disease or condition associated with abnormal laminin binding is junctional epidermolysis bullosa or nephrotic syndrome.

DETAILED DESCRIPTION

Figure 1:
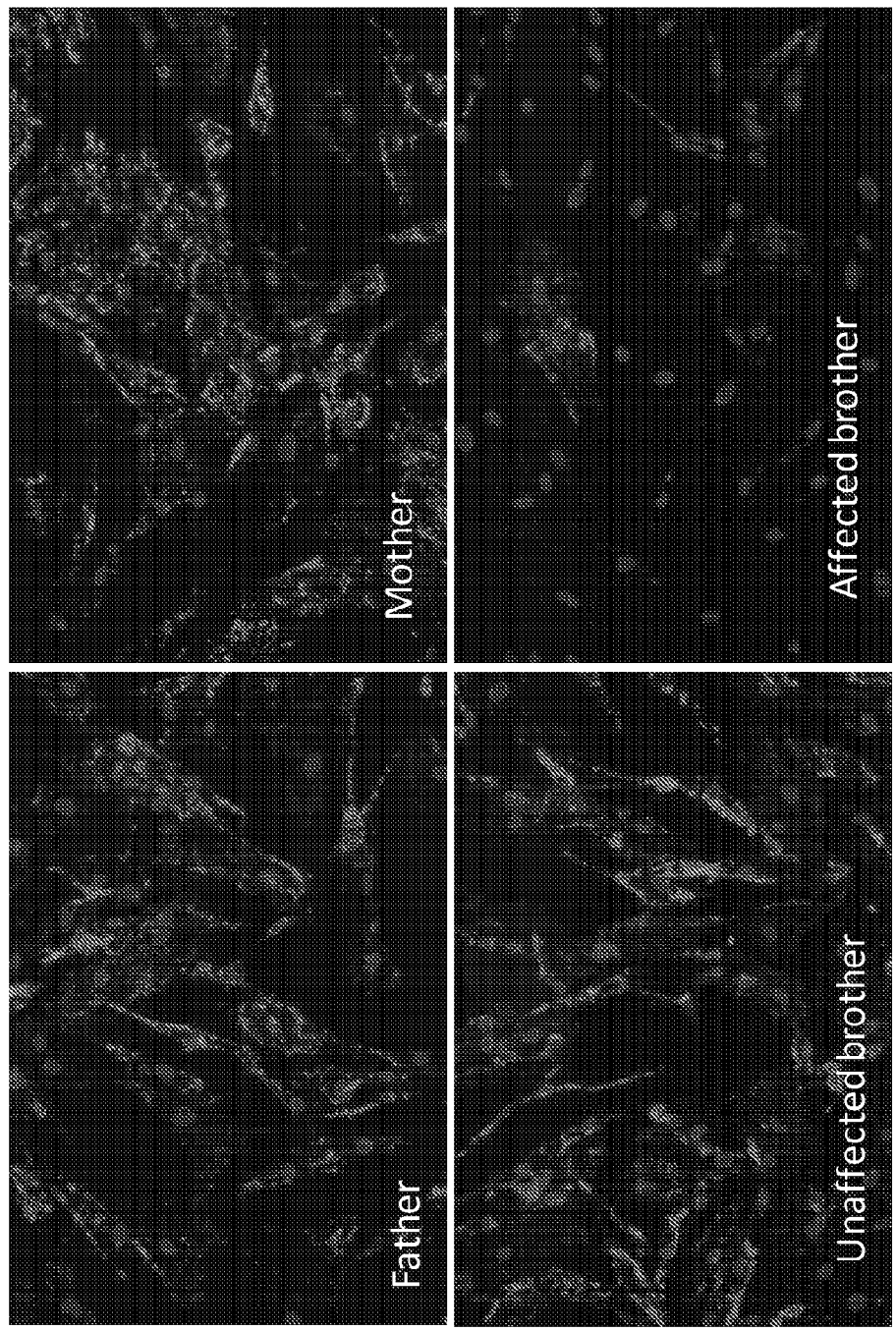
FIG. 1. The bottom right image shows fibroblasts from a child affected with CMD. Top images and bottom left image show fibroblasts from unaffected family members of a CMD affected child. Laminin levels are labeled with rabbit anti-laminin antibodies. Nuclei are stained with DAPI.
Figure 2:
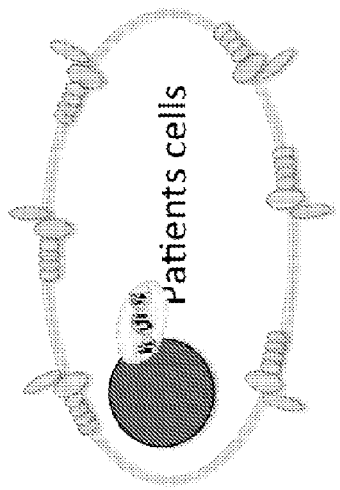
FIG. 2. Laminin binds to glycosylated lipids on the surface of a cell. Normal glycosylation of cell surface lipids allows fibroblasts to bind to laminin. Fibroblasts in muscular dystrophy patients are defective in glycosylation, and hence, are unable to bind to laminin.
Figure 2:
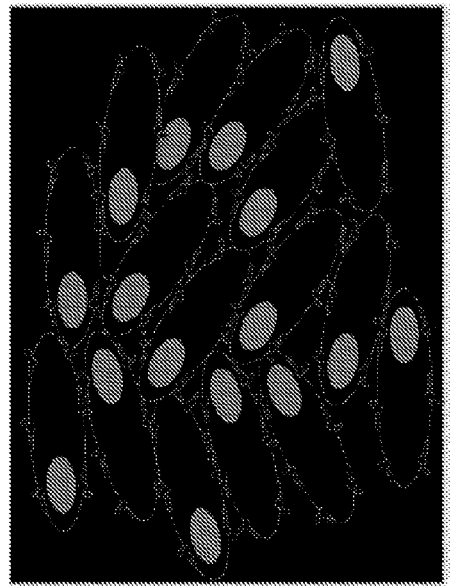
Figure 2:
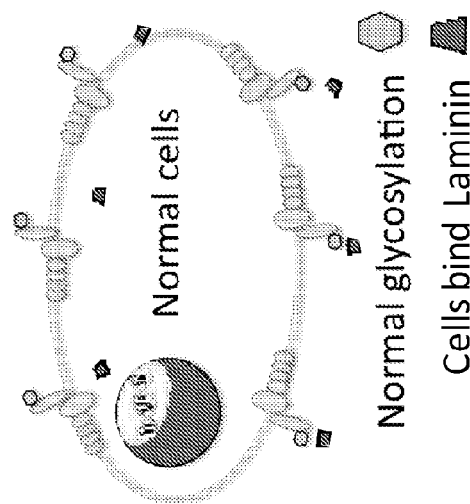
Figure 2:
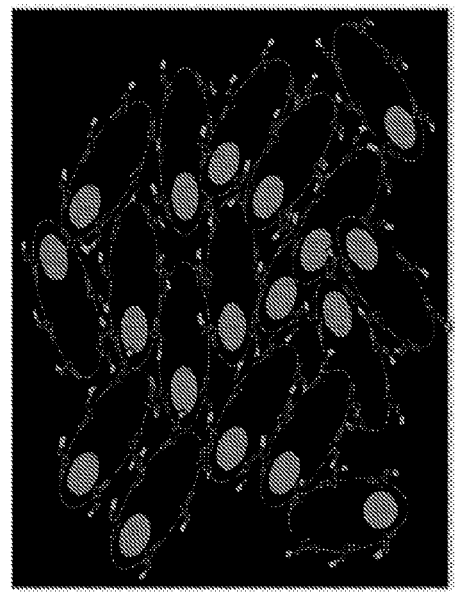
Figure 3:
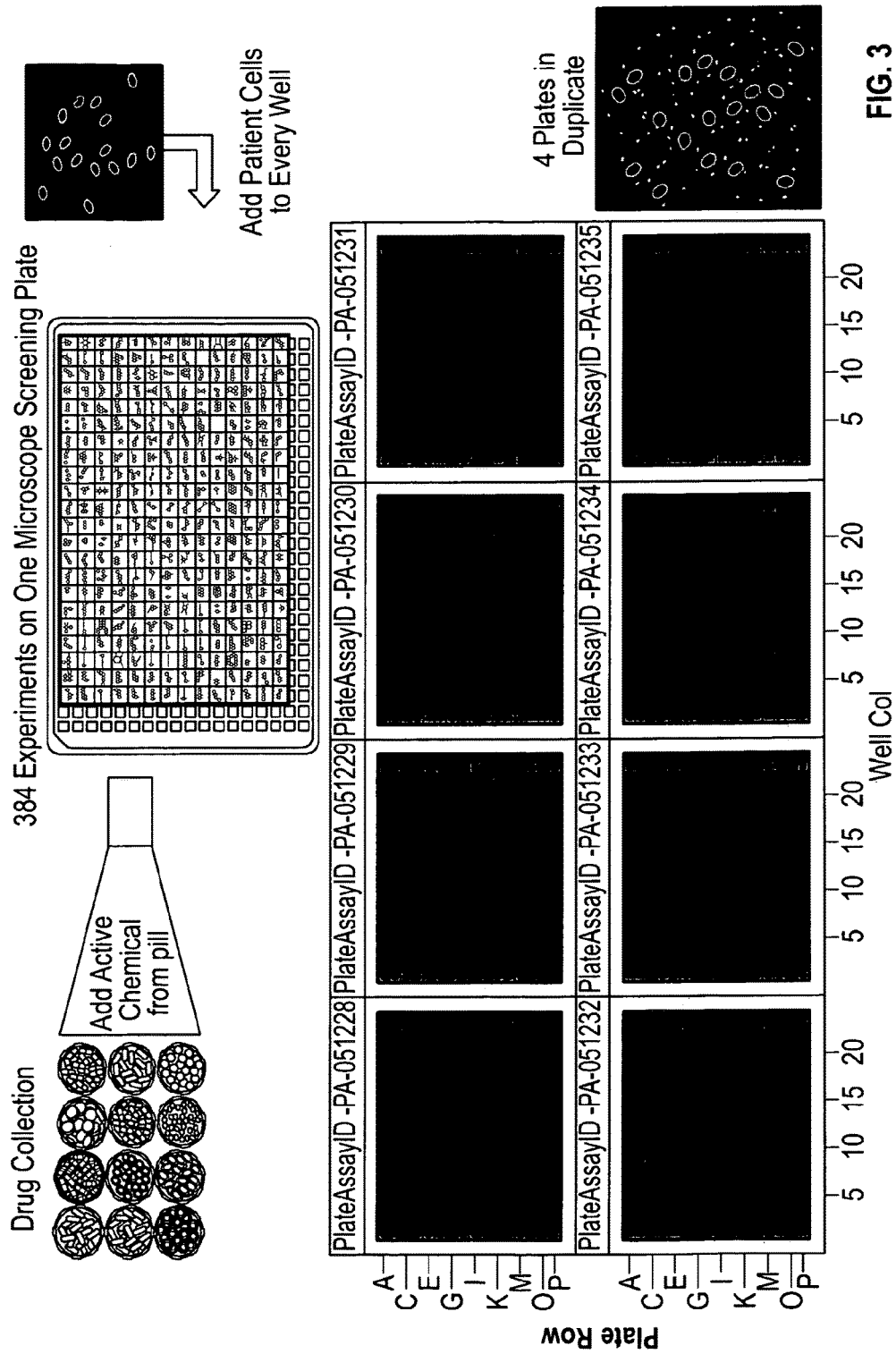
FIG. 3. Cells from a rare disease patient are added to each well of a 384-well plate. A different active drug or nutraceutical was added to each well. Laminin was labeled with rabbit anti-laminin antibodies. Plates were scanned by an automated confocal microscope. Experiments were performed on 4 plates in duplicate.
Figure 4:
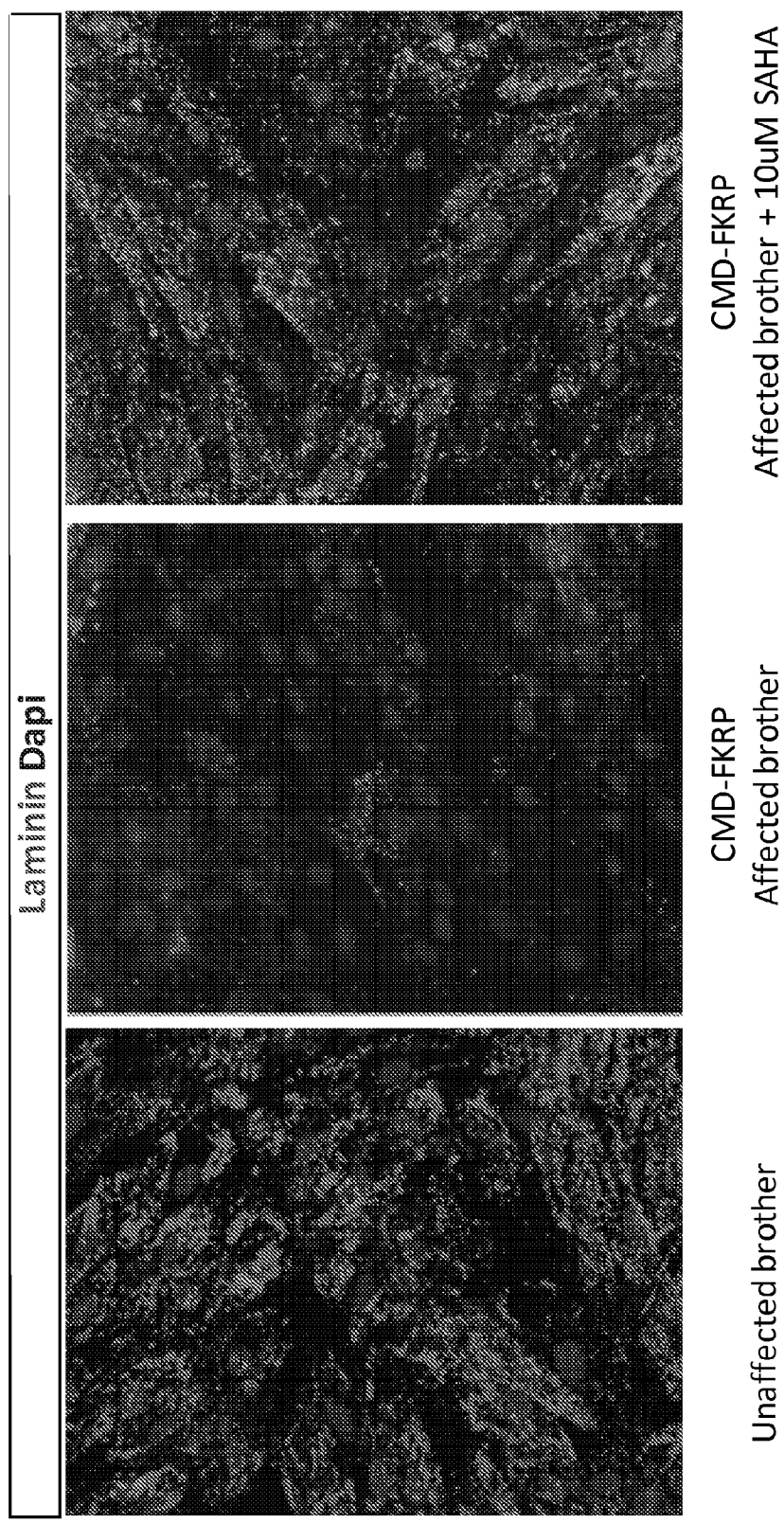
FIG. 4. Fibroblasts from a CMD-affected patient (middle) are markedly lower in laminin binding, as compared to the patient's unaffected brother (left). Once the patient's fibroblasts are treated with SAHA, a hit identified in the screen, laminin binding is normalized to the levels of the patient's unaffected brother. Laminin was labeled with rabbit anti-laminin antibodies. Nuclei are stained with DAPI.
Figure 5:
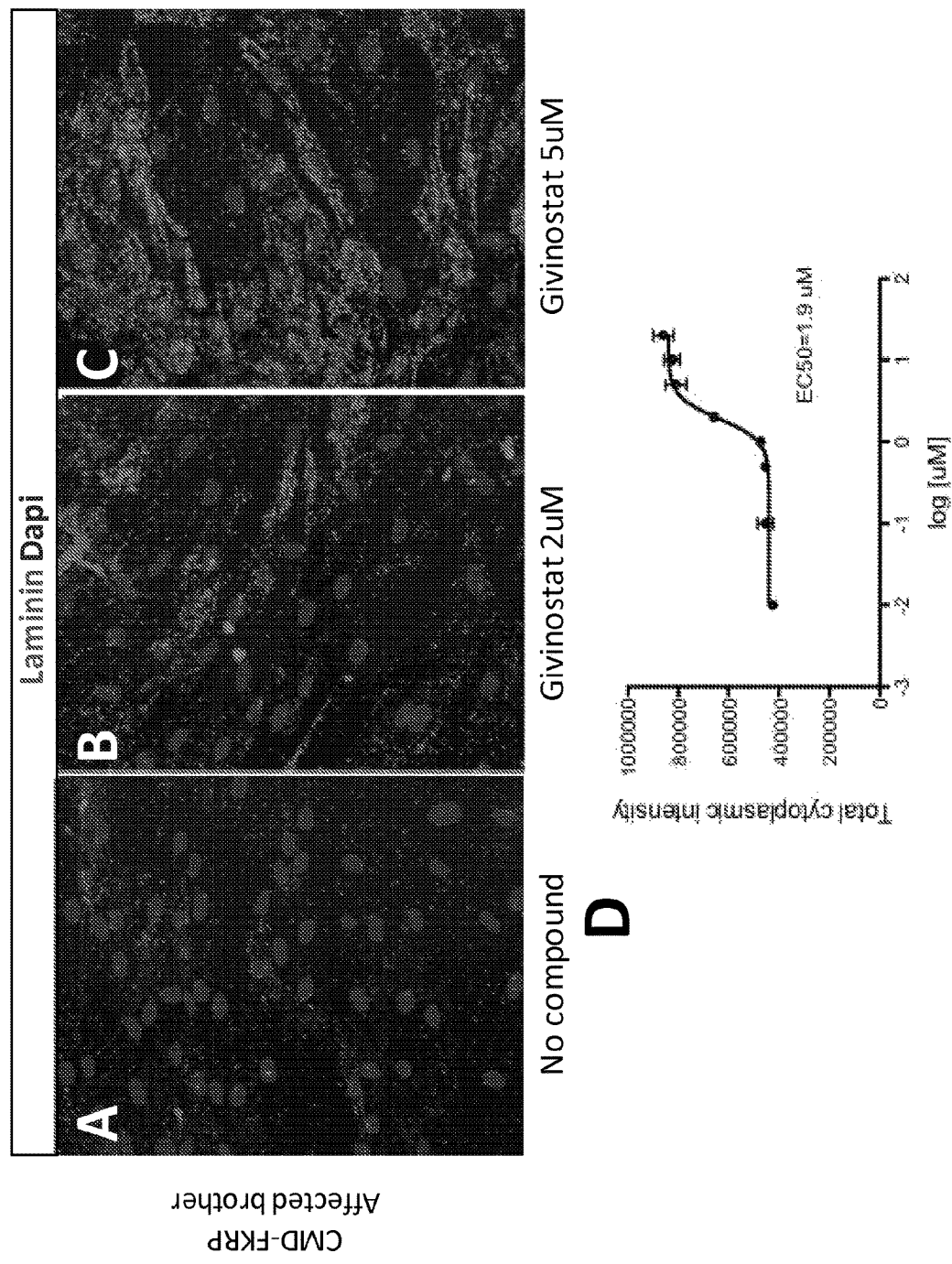
FIG. 5. Immortalized fibroblasts from a CMD patient display increased levels of laminin binding upon treatment with Givinostat an HDAC inhibitor, structurally similar to those identified in the screen as "hits" from an HCS. A dose response curve for Givinostat was prepared measuring laminin staining intensity at various concentrations of the compound. Laminin was labeled with rabbit anti-laminin antibodies. Nuclei are stained with DAPI.
Figure 6:
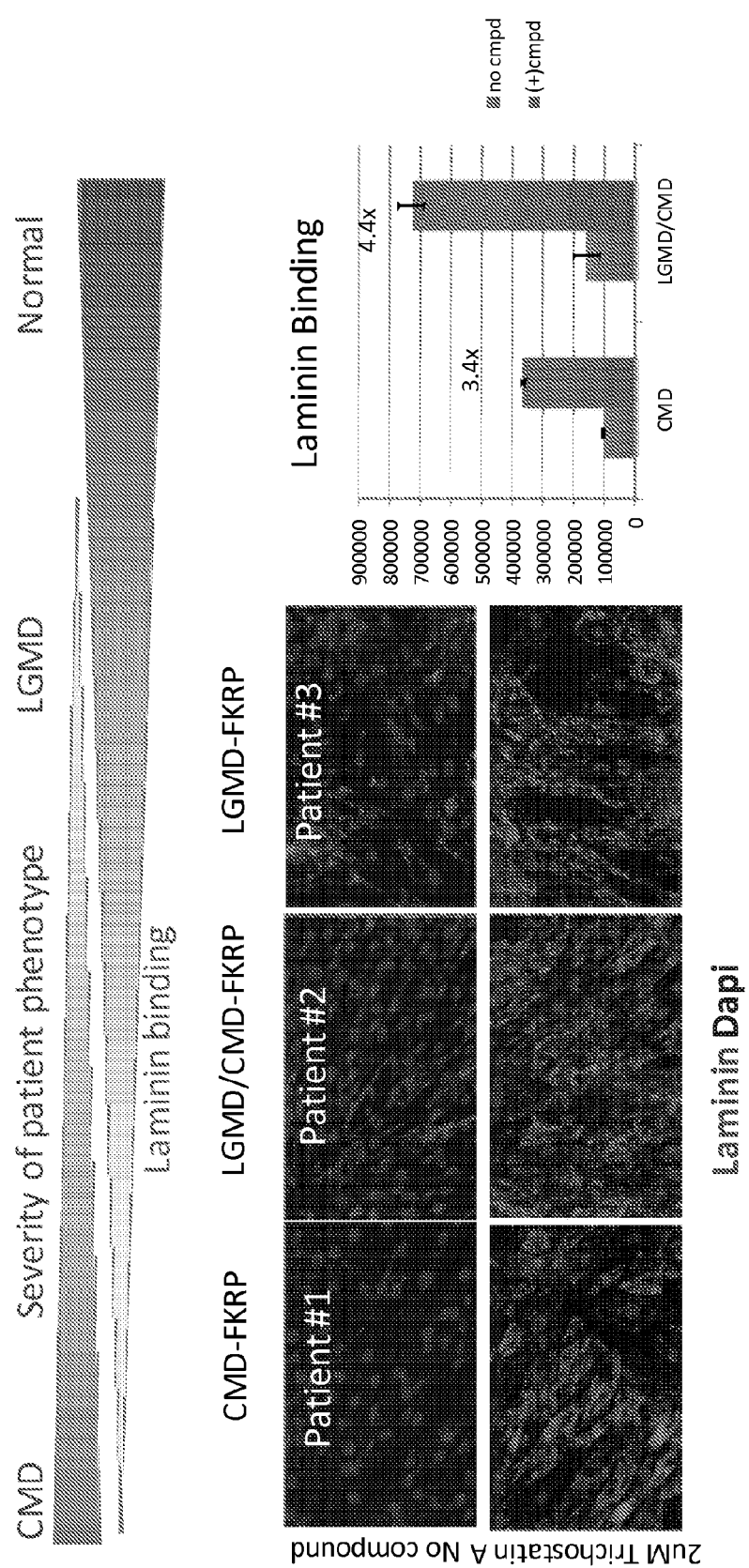
FIG. 6. Fibroblasts were obtained from CMD patients with either low (CMD-FKRP) laminin binding, mid-range laminin binding (LGMD/CMD-FKRP), or closer to normal (LGMD-FKRP) laminin binding. Trichostatin A, identified as a "hit" by the HSC screens described herein, increased laminin binding in fibroblasts with various levels of laminin binding deficiency. Laminin was labeled with rabbit anti-laminin antibodies. Nuclei are stained with DAPI.
Figure 7:
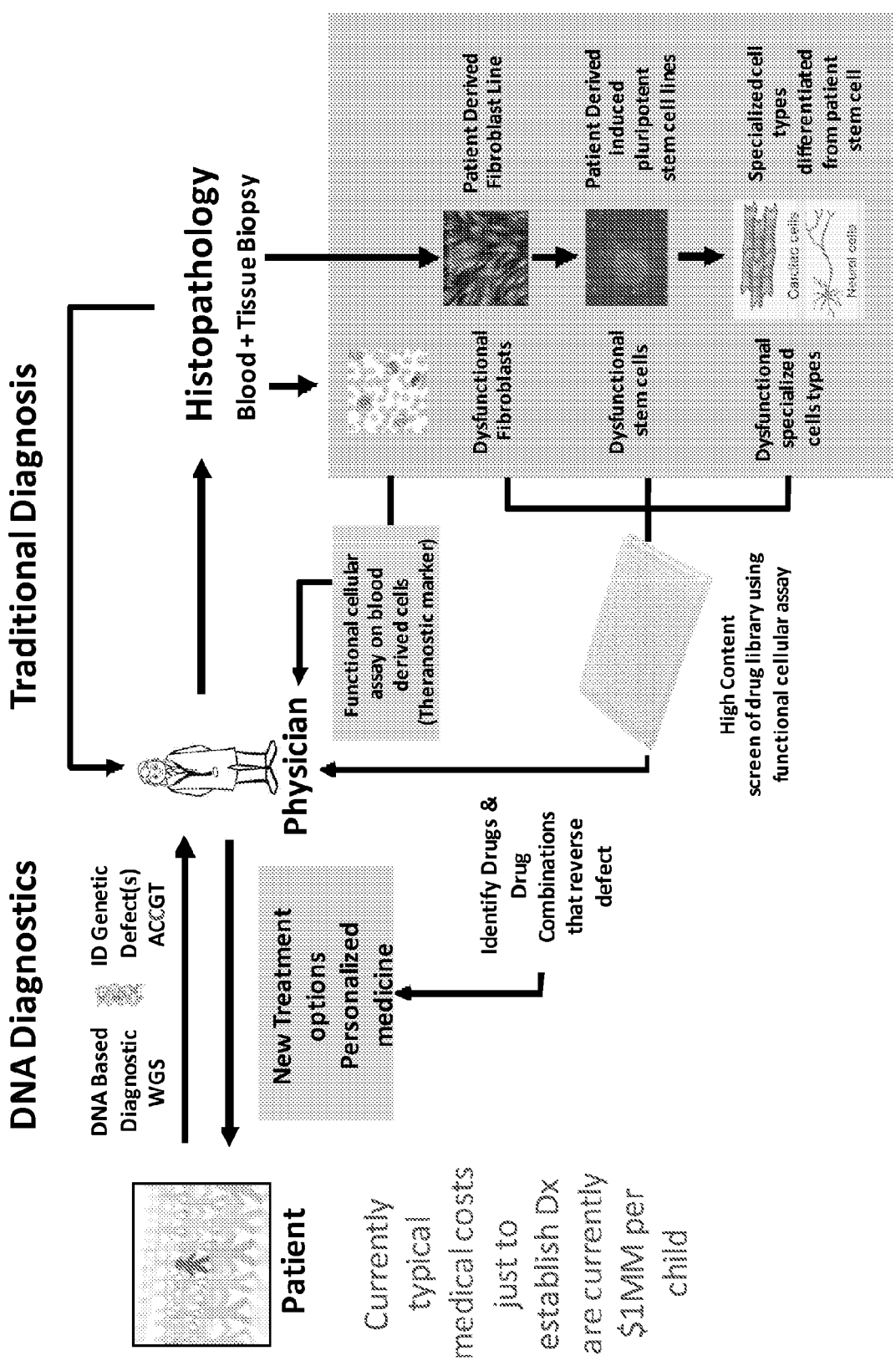
FIG. 7. This figure exemplifies methods by which various dysfunctional cell types in a rare disease patient can be studied with the methods and platforms disclosed herein in order to identify drugs and drug combinations that will reverse an optically visible rare disease phenotype in each separate cell type.
Figure 8:
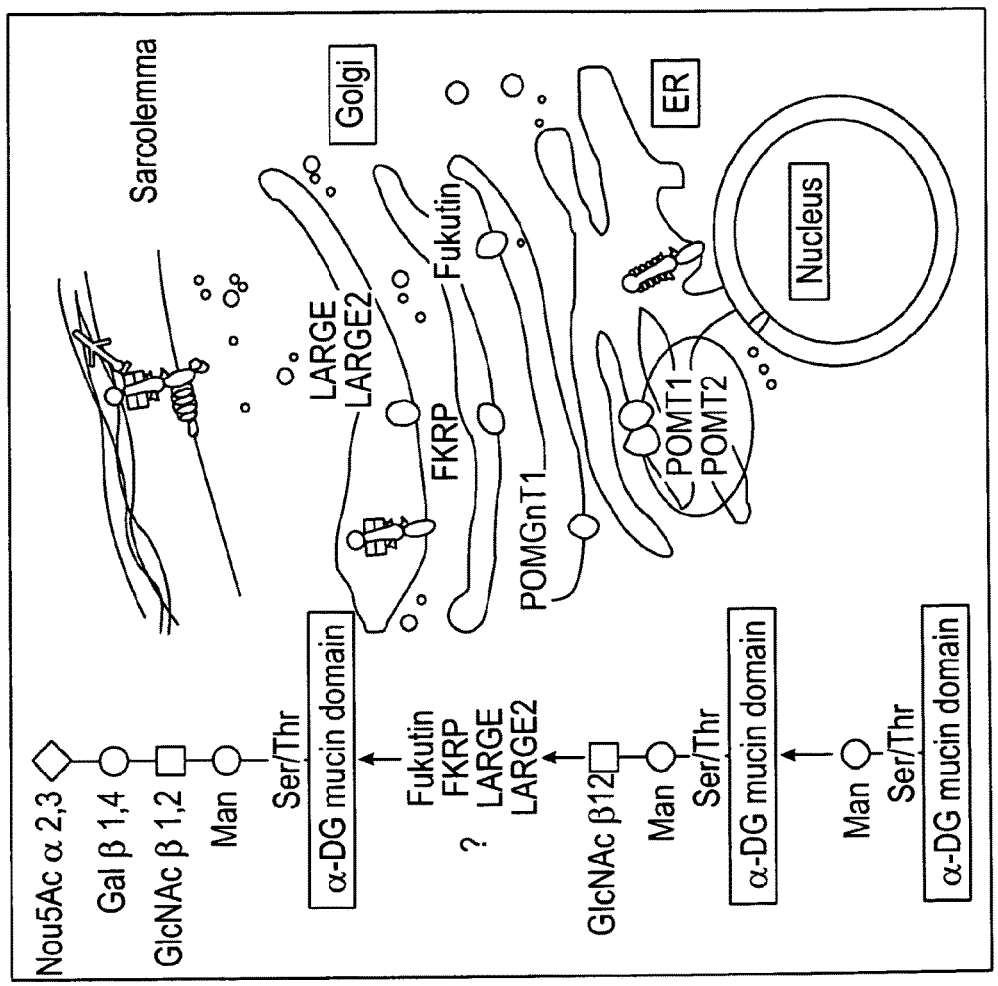
FIG. 8. Fibroblasts from a CMD patient with two deficient copies of the POMT1 gene show visibly reduced laminin binding as compared to the patient's heterozygous mother, who carries only one deficient copy of POMT1. Laminin is labeled with rabbit anti-laminin antibodies. Nuclei are stained with DAPI.
Figure 8:
Figure 8:
Figure 9:
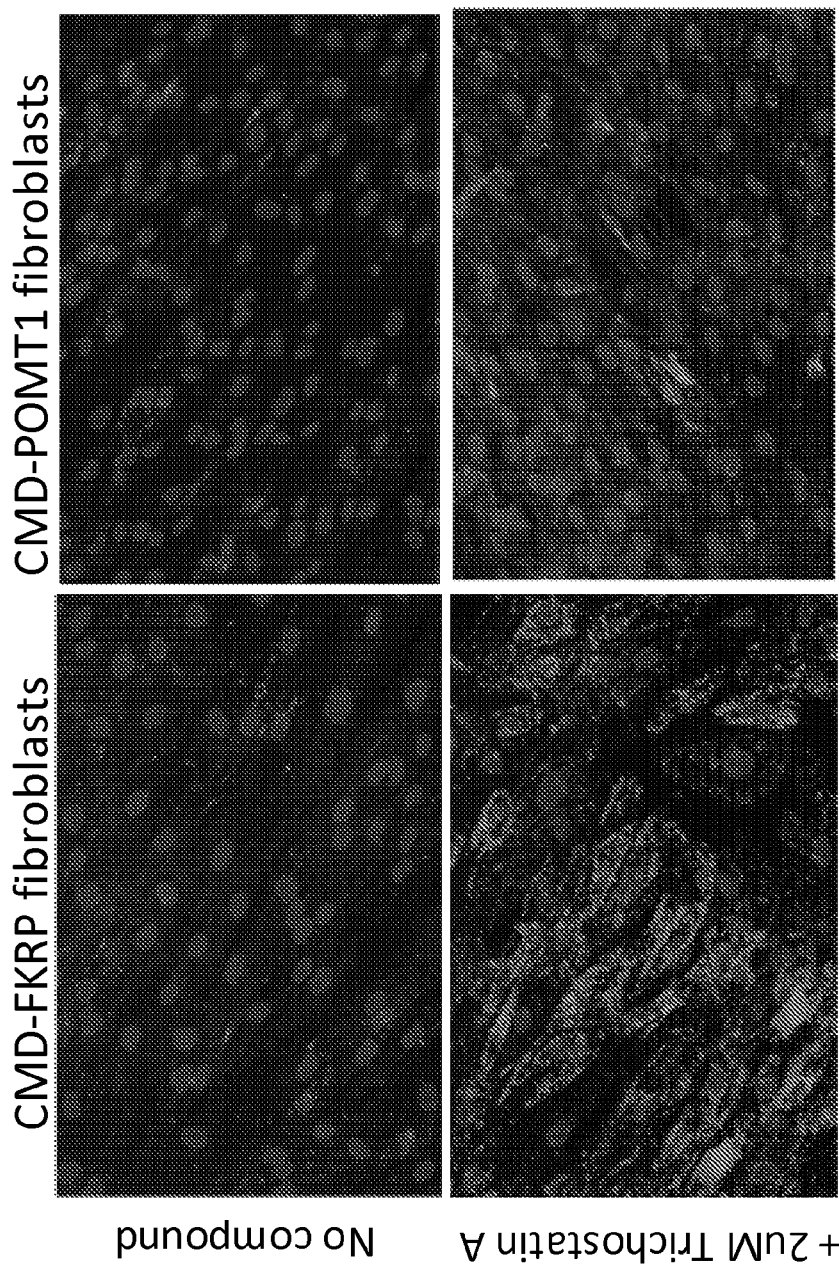
FIG. 9. Fibroblasts were taken from an FKRP deficient CMD patient and a POMT1 deficient CMD patient. Addition of Trichostatin A resulted in increased laminin binding in fibroblasts from the CMD-FKRP patient; however, this compound did not result in visibly increased laminin binding in fibroblasts from the CMD-POMT1 patient. Laminin is labeled with rabbit anti-laminin antibodies. Nuclei are stained with DAPI.
Figure 10:
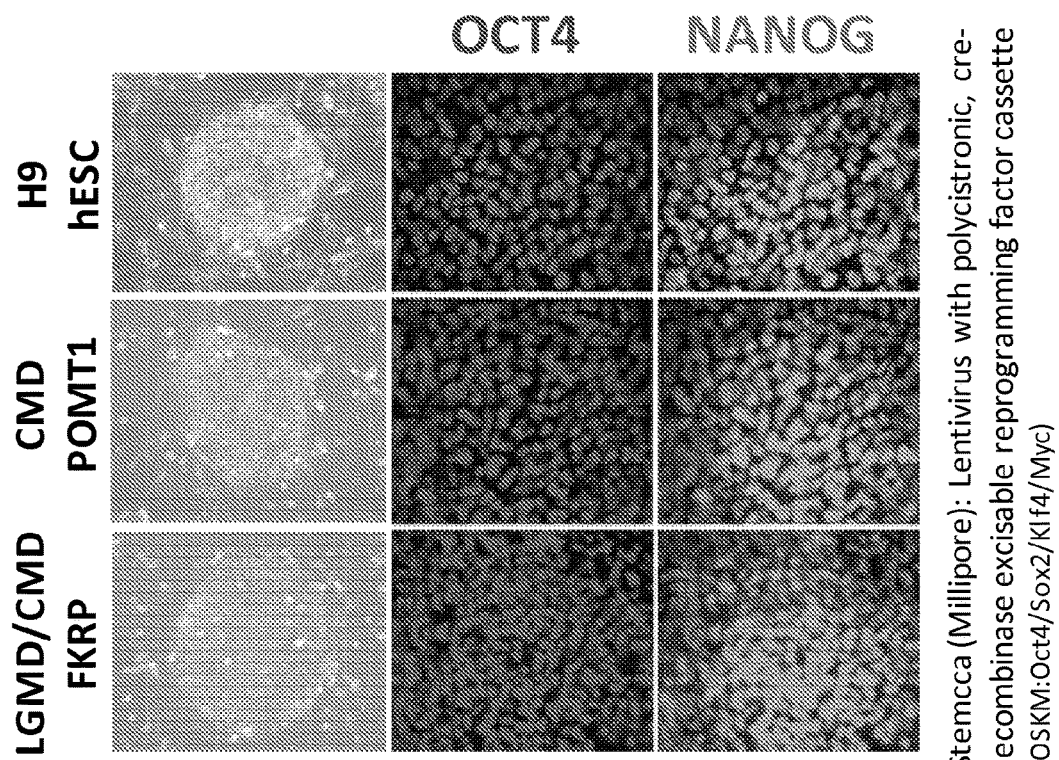
FIG. 10. iPSC cell lines were generated by obtaining fibroblasts from a LGMD/CMD-FKRP patient and a CMD-POMT1 patient. The fibroblasts were transfected with polycistronic lentiviral cassettes expressing OCT4. Each cell line expressed OCT4 and NANOG markers of cell dedifferentiation at a level similar to that of the H9 human embryonic stem cell (hESC) line.

It is estimated that bringing a new drug to market can take about 15 years and cost about $800 million. A significant portion of this time and cost results from the need to generate pharmacokinetic and safety data for the approval process. Due to the high costs associated with bringing new drugs to market and limited resources, companies often focus on commercializing drugs that will provide the highest return on investment. As a result of this focus, limited funds and resources are allocated to investigating treatments for rare diseases. There is a significant unmet need for novel and efficacious treatments for rare diseases that can be brought to market quickly and inexpensively. There are currently thousands of known drugs and nutraceuticals, for which pharmacokinetic and safety data has previously been generated. Repurposing these drugs and nutraceuticals satisfies the unmet need for treatments for rare diseases in a cost-effective manner.

There is a need for novel methods and platforms for identifying known drugs and nutraceuticals for repurposing to treat rare diseases. These methods should be fast, personalizable, and reduce the costs and steps associated with identifying known drugs/nutraceuticals for repurposing. Certain rare diseases are associated with optically-visible cell phenotypes. As opposed to traditional biochemical assays, phenotypic screens based on optically-visible phenotypes enable medical professionals to visualize (a) the phenotypic response of a known drug/nutraceutical and (b) the whole cell effects (e.g., toxicity and dose response) of the known drug/nutraceutical. The simultaneous production of biochemical and whole cell data reduces the time, number of assays, and costs needed to identify known drugs/nutraceuticals that may be repurposed to treat rare diseases. Utilizing High Content Screening further reduces the time needed to identify known drugs/nutraceuticals that are repurposed to treat rare diseases. Disclosed herein, are methods and platforms that satisfy the aforementioned needs.

Theranostics Platforms

The platforms disclosed herein identify drug and/or nutraceutical candidates for normalizing, or partially normalizing, a rare-disease associated with an optically-visible cell phenotype. The drug/nutraceutical library includes known drugs, metabolites of known drugs, and/or nutraceuticals. Examples of cell phenotypes that are, or in the alternative are made optically-visible, include cell morphology, nuclear morphology, morphology of the plasma membrane, the morphology of any cytosolic organelle. Where the cell phenotype is not naturally optically-visible, the phenotype is rendered optically-visible due to the use of an optically-visible dye/label (e.g., a fluorescent dye). Individuals that will benefit from these platforms are symptomatic (including those with limited symptoms), or asymptomatic.

The platforms comprise a rare disease cell with an optically-visible cell phenotype, and a means for visualizing the response of a cell having an optically-visible rare-disease cell phenotype to a drug or nutraceutical from the drug/nutraceutical library to identify drug/nutraceutical hits. The platforms are optionally used to establish dose-response curves for the hits. The platforms also optionally include genotyping individuals to determine if they would benefit from the platforms, for example to determine which strain of a rare disease an individual has, what disease an individual has, if an individual is predisposed to develop a rare disease.

The means for visualizing the response of a cell having an optically-visible rare-disease cell phenotype to a drug or nutraceutical from the drug/nutraceutical library is optionally a microscope with sufficient magnifying power to visualize one cell in a plurality of cells. The images captured by the microscope are optionally stored in electronic memory. The microscope is optionally part of a High Content Screening (HCS) system with automated liquid handling and automated plate handling, image analysis software. The system optionally has software that analyzes degrees of response of the cells to a drug or nutraceutical and dose-response curves.

Any hits identified by these platforms are used to create a Rare Disease Specific Drug Library for the rare disease. The Rare Disease Specific Drug Library is optionally further personalized for each individual with the rare disease, for example some drugs will be eliminated, and/or different drug combinations/dosages will be identified for each individual.

The cells for use with the platforms are optionally naturally-occurring cells obtained from a subject with a rare disease cell phenotype, cells derived from stem cells obtained from a subject with a rare disease cell phenotype, or cells derived from iPS cells produced from cells from a subject with a rare disease cell phenotype. The cells are optionally recombinant cells. In some alternatives, the cells are derived from a personalized cell line established from an individual with an optically-visible rare-disease cell phenotype. In other alternatives, the cells are derived from a general cell line established from a cell obtained from a donor individual with an optically-visible rare-disease cell phenotype. The platforms optionally include a cell from a naturally occurring cell line, a cell obtained from differentiating a stem cell/iPS cell taken from an individual with a rare disease, and/or a recombinant cell.

In some alternatives, the rare diseases are associated with one or more biomarkers. If the rare disease is associated with a biomarker, the biomarker is utilized to determine if a treatment for a rare disease is successful, the systemic effects of a treatment, or the dose response of a treatment.

Exemplary Rare Disease Theranostic Platforms

Multiple Rare Disease Theranostics Platforms are created from combinations of any of the elements disclosed herein. Exemplary, and non-limiting, Rare Disease Theranostics Platforms include the following.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); and (c) a means for visualizing the response of a cell with optically-visible rare-disease cell phenotype to a drug or nutraceutical from the drug/nutraceutical library.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; and (d) a computer-implemented system (e.g., computer software or a computer algorithm) for analyzing the response of an optically-visible rare-disease cell phenotype to a drug or nutraceutical from the drug/nutraceutical library.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; and (d) a means for genotyping an individual (e.g., a symptomatic or asymptomatic individual) to determine whether they have a Rare Disease and/or what strain of a Rare Disease they have.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; and (d) a biomarker associated with the rare disease.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell with optically-visible rare-disease cell phenotype to a drug or nutraceutical from the drug/nutraceutical library; and (d) a cell with optically-visible rare-disease cell phenotype obtained (or, differentiated) from a stem cell taken from an individual with the rare disease.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; (d) a computer-implemented system (e.g., computer software or a computer algorithm) for analyzing the response of an optically-visible rare-disease cell phenotype to a drug or nutraceutical from the drug/nutraceutical library; and (e) a means for genotyping an individual (e.g., a symptomatic or asymptomatic individual) to determine whether they have a Rare Disease and/or what strain of a Rare Disease they have.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; (d) a computer-implemented system (e.g., computer software or a computer algorithm) for analyzing the response of an optically-visible rare-disease cell phenotype to a drug or nutraceutical from the drug/nutraceutical library; and (e) a biomarker associated with the rare disease.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; (d) a computer-implemented system (e.g., computer software or a computer algorithm) for analyzing the response of an optically-visible rare-disease cell phenotype to a drug or nutraceutical from the drug/nutraceutical library; and (e) a cell with optically-visible rare-disease cell phenotype obtained (or, differentiated) from a stem cell taken from an individual with the rare disease.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; (d) a means for genotyping an individual (e.g., a symptomatic or asymptomatic individual) to determine whether they have a Rare Disease and/or what strain of a Rare Disease they have; and (e) a biomarker associated with the rare disease.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; (d) a means for genotyping an individual (e.g., a symptomatic or asymptomatic individual) to determine whether they have a Rare Disease and/or what strain of a Rare Disease they have; and (e) a cell with optically-visible rare-disease cell phenotype obtained (or, differentiated) from a stem cell taken from an individual with the rare disease.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; (d) a biomarker associated with the rare disease; and (e) a cell with optically-visible rare-disease cell phenotype obtained (or, differentiated) from a stem cell taken from an individual with the rare disease.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; (d) a computer-implemented system (e.g., computer software or a computer algorithm) for analyzing the response of an optically-visible rare-disease cell phenotype to a drug or nutraceutical from the drug/nutraceutical library; (e) a means for genotyping an individual (e.g., a symptomatic or asymptomatic individual) to determine whether they have a Rare Disease and/or what strain of a Rare Disease they have; and (f) a biomarker associated with the rare disease.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; (d) a computer-implemented system (e.g., computer software or a computer algorithm) for analyzing the response of an optically-visible rare-disease cell phenotype to a drug or nutraceutical from the drug/nutraceutical library; (e) a means for genotyping an individual (e.g., a symptomatic or asymptomatic individual) to determine whether they have a Rare Disease and/or what strain of a Rare Disease they have; and (f) a cell with optically-visible rare-disease cell phenotype obtained (or, differentiated) from a stem cell taken from an individual with the rare disease.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; (d) a means for genotyping an individual (e.g., a symptomatic or asymptomatic individual) to determine whether they have a Rare Disease and/or what strain of a Rare Disease they have; (e) a biomarker associated with the rare disease; and (f) a cell with optically-visible rare-disease cell phenotype obtained (or, differentiated) from a stem cell taken from an individual with the rare disease.

A rare disease theranostics platform, comprising: (a) a rare disease with an optically-visible cell phenotype (i.e., an Optically-Visible Rare Disease Cell Phenotype); (b) a drug/nutraceutical library (e.g., a Drug/Nutraceutical Library or a Rare Disease Specific Drug/Nutraceutical Library); (c) a means for visualizing the response of a cell having an optically-visible rare-disease cell phenotype to a drug or nutraceutical from the drug/nutraceutical library; (d) a computer-implemented system (e.g., computer software or a computer algorithm) for analyzing the response of an optically-visible rare-disease cell phenotype to a drug or nutraceutical from the drug/nutraceutical library; (e) a means for genotyping an individual (e.g., a symptomatic or asymptomatic individual) to determine whether they have a Rare Disease and/or what strain of a Rare Disease they have; (f) a biomarker associated with the rare disease; and (g) a cell with optically-visible rare-disease cell phenotype obtained (or, differentiated) from a stem cell taken from an individual with the rare disease.

Methods of Identifying Drug and/or Nutraceutical Candidates

The methods disclosed herein identify drug and/or nutraceutical candidates for normalizing, or partially normalizing, a rare-disease associated with an optically-visible cell phenotype. The drug/nutraceutical library includes known drugs, metabolites of known drugs, and/or nutraceuticals. Examples of cell phenotypes that are, or in the alternative are made optically-visible, include cell morphology, nuclear morphology, morphology of the plasma membrane, the morphology of any cytosolic organelle. Where the cell phenotype is not naturally optically-visible, the phenotype is rendered optically-visible due to the use of an optically-visible dye/label (e.g., a fluorescent dye). Individuals that will benefit from these methods and methods are symptomatic (including those with limited symptoms), or asymptomatic.

The methods comprise identifying a rare disease cell with an optically-visible cell phenotype, and visualizing the response of a cell having an optically-visible rare-disease cell phenotype to a drug or nutraceutical from the drug/nutraceutical library to identify drug/nutraceutical hits. The methods are optionally used to establish dose-response curves for the hits. The methods also optionally include genotyping individuals to determine if they would benefit from the methods and methods, for example to determine which strain of a rare disease an individual has, what disease an individual has, if an individual is predisposed to develop a rare disease.

Visualizing the response of a cell having an optically-visible rare-disease cell phenotype to a drug or nutraceutical from the drug/nutraceutical library is optionally done with a microscope with sufficient magnifying power to visualize one cell in a plurality of cells. The images captured by the microscope are optionally stored in electronic memory. The microscope is optionally part of a High Content Screening (HCS) system with automated liquid handling and automated plate handling, image analysis software. The system optionally has software that analyzes degrees of response of the cells to a drug or nutraceutical and dose-response curves.

Any hits identified by these methods are used to create a Rare Disease Specific Drug Library for the rare disease. The methods optionally further include personalizing the Rare Disease Specific Drug Library for each individual with the rare disease, for example some drugs will be eliminated, and/or different drug combinations/dosages will be identified for each individual.

The cells for use with the methods are optionally naturally-occurring cells obtained from a subject with a rare disease cell phenotype, cells derived from stem cells obtained from a subject with a rare disease cell phenotype, or cells derived from iPS cells produced from cells from a subject with a rare disease cell phenotype. The cells are optionally recombinant cells. In some alternatives, the methods include deriving cells from a personalized cell line established from an individual with an optically-visible rare-disease cell phenotype. In other alternatives, the methods include deriving the cell from a general cell line established from a cell obtained from a donor individual with an optically-visible rare-disease cell phenotype. The methods optionally utilize a cell from a naturally occurring cell line, a cell obtained from differentiating a stem cell/iPS cell taken from an individual with a rare disease, and/or a recombinant cell.

In some alternatives, the rare diseases are associated with one or more biomarkers. If the rare disease is associated with a biomarker, the methods optionally include utilizing the biomarker to determine if a treatment for a rare disease is successful, the systemic effects of a treatment, or the dose response of a treatment.

Exemplary Methods

Multiple methods are created from combinations of any of the elements disclosed herein. Exemplary, and non-limiting, methods include the following.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; and (c) analyzing the visualized cells to determine the response of the plurality of cells to the drug or nutraceutical from the drug/nutraceutical library.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; and (d) identifying the optically-visible rare-disease cell phenotype associated with the rare disease.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; and (d) genotyping an individual (e.g., a symptomatic or asymptomatic individual) to determine whether they have a Rare Disease and/or what strain of a Rare Disease they have.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; and (d) identifying and analyzing a biomarker associated with the rare disease.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; and (d) differentiating a stem cell taken from an individual with the rare disease into a cell with optically-visible rare-disease cell phenotype suitable for use with the method.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; (d) identifying the optically-visible rare-disease cell phenotype associated with the rare disease; and (e) genotyping an individual (e.g., a symptomatic or asymptomatic individual) to determine whether they have a Rare Disease and/or what strain of a Rare Disease they have.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; (d) identifying the optically-visible rare-disease cell phenotype associated with the rare disease; and (e) identifying and analyzing a biomarker associated with the rare disease.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; (d) identifying the optically-visible rare-disease cell phenotype associated with the rare disease; and (e) differentiating a stem cell taken from an individual with the rare disease into a cell with optically-visible rare-disease cell phenotype suitable for use with the method.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; (d) genotyping an individual (e.g., a symptomatic or asymptomatic individual) to determine whether they have a Rare Disease and/or what strain of a Rare Disease they have; and (e) identifying and analyzing a biomarker associated with the rare disease.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; (d) genotyping an individual (e.g., a symptomatic or asymptomatic individual) to determine whether they have a Rare Disease and/or what strain of a Rare Disease they have; and (e) differentiating a stem cell taken from an individual with the rare disease into a cell with optically-visible rare-disease cell phenotype suitable for use with the method.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; (d) identifying and analyzing a biomarker associated with the rare disease; and (e) differentiating a stem cell taken from an individual with the rare disease into a cell with optically-visible rare-disease cell phenotype suitable for use with the method.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; (d) genotyping an individual (e.g., a symptomatic or asymptomatic individual) to determine whether they have a Rare Disease and/or what strain of a Rare Disease they have; (e) identifying and analyzing a biomarker associated with the rare disease; and (f) differentiating a stem cell taken from an individual with the rare disease into a cell with optically-visible rare-disease cell phenotype suitable for use with the method.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; (d) identifying the optically-visible rare-disease cell phenotype associated with the rare disease; (e) genotyping an individual (e.g., a symptomatic or asymptomatic individual) to determine whether they have a Rare Disease and/or what strain of a Rare Disease they have; and (f) differentiating a stem cell taken from an individual with the rare disease into a cell with optically-visible rare-disease cell phenotype suitable for use with the method.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; (d) identifying the optically-visible rare-disease cell phenotype associated with the rare disease; (e) genotyping an individual (e.g., a symptomatic or asymptomatic individual) to determine whether they have a Rare Disease and/or what strain of a Rare Disease they have; and (f) identifying and analyzing a biomarker associated with the rare disease.

A method of identifying a drug or nutraceutical candidate for normalizing, or partially normalizing, an optically-visible rare-disease cell phenotype in a subject in need thereof, comprising the steps of: (a) contacting a plurality of cells with the optically-visible rare-disease cell phenotype with a drug or nutraceutical from a drug/nutraceutical library; (b) visualizing the plurality of cells following contact with the drug or nutraceutical from the drug/nutraceutical library; (c) analyzing the visualized cells to determine the response of the plurality of cells to the drug or nutraceutical from the drug/nutraceutical library; (d) identifying the optically-visible rare-disease cell phenotype associated with the rare disease; (e) genotyping an individual (e.g., a symptomatic or asymptomatic individual) to determine whether they have a Rare Disease and/or what strain of a Rare Disease they have; (f) identifying and analyzing a biomarker associated with the rare disease; and (g) differentiating a stem cell taken from an individual with the rare disease into a cell with optically-visible rare-disease cell phenotype suitable for use with the method.

Certain Definitions

As used herein, "theranostic platform" means a system for identifying, validating, and/or optimizing a drug or nutraceutical for the treatment of a disease. In some embodiments, the theranostic platform is used in personalized medicine, i.e., it is used to identify, validate, and/or optimize a drug or nutraceutical for the treatment of a specific disease (e.g., a specific disease subtype) in a specific individual.

As used herein, a "known drug" means any drug that is currently being used for human or veterinary use, has been used for human or veterinary use, and has been studied by medical professionals in a clinical setting (e.g., a clinical trial, e.g., a phase I clinical trial, a phase II clinical trial, a phase III clinical trial, a phase IV clinical trial). Examples of known drugs include, but are not limited to, drugs approved by a national regulatory agency (e.g., the United States Federal Drug Administration (FDA), the European Medicines Agency, the UK Medicines and Healthcare Products Regulatory Agency, the Therapeutic Products Directorate (TPD) of Health Canada, the Australian Therapeutic Goods Administration, the Chinese State Food and Drug Administration, the Japanese Pharmaceuticals and Medical Devices Agency) as an over-the-counter medicine or a prescription medicine, drugs classified as GRAS/E (Generally Regarded as Safe and Effective) by the US FDA, drugs listed in the US FDA Orange Book, drugs listed in any edition of the Physicians' Desk Reference (PDR), drugs listed in any edition of the American Hospital Formulary Service Drug Information (AHFS DI), drugs listed in the Merck Index, or any combination thereof.

As used herein, "nutraceutical" means a product isolated or purified from a food that produces a physiological benefit or provides protection against a disease. Non-limiting examples of nutraceuticals include: vitamins, minerals, herbs or other botanicals (e.g., those used in traditional Chinese Medicine, e.g., ginger, garlic), amino acids, enzymes, metabolites, antioxidants (e.g., resveratrol; flavonoids; anthocyanins), isoflavanoids, organosulfur compounds (e.g., sulforaphane), omega 3 fatty acids (e.g., alpha-linolenic acid), and functional foods (i.e., enriched foods, e.g., milk supplemented with vitamin D).

The terms "individual," "patient," or "subject" are used interchangeably. As used herein, they mean any mammal (i.e. species of any orders, families, and genus within the taxonomic classification animalia: chordata: vertebrata: mammalia). In some embodiments, the mammal is a human. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The terms "administer," "administering", "administration," and the like, as used herein, refer to the methods that may be used to enable delivery of agents or compositions to the desired site of biological action. These methods include, but are not limited to parenteral injection (e.g., intravenous, subcutaneous, intraperitoneal, intramuscular, intravascular, intrathecal, intravitreal, infusion, or local). Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

As used herein, "normalize" means to bring a cell phenotype to a normal condition or state, e.g., to change a diseased cell phenotype to a wild-type phenotype.

As used herein, "partially normalize" means to bring a cell phenotype to a partially normal condition or state, e.g., to change a diseased cell phenotype to a state or condition that is closer to a wild-type phenotype.

Rare Diseases

Disclosed herein, in certain embodiments, are methods of identifying a drug or nutraceutical candidate for normalizing, or partially normalizing, an optically-visible rare-disease cell phenotype in a subject in need thereof. Further disclosed herein, in certain embodiments, are rare disease theranostics platforms.

As used herein, a "rare disease" (or "orphan disease") means (a) any disease that affects a small percentage of a population, or (b) any neglected disease. As used herein, "population" means any group of individuals (e.g., the global population, a national population, a city population, or an ethnic group). In some embodiments, a rare disease varies in prevalence between populations. For example, cystic fibrosis is a rare disease in Asian populations.

In some embodiments, the rare disease affects less than 200,000 persons in a population in the United States. In some embodiments, a rare disease affects less than about 1 in 1,500 people. In some embodiments, a rare disease affects less than about 1 in 2,000 people. In some embodiments, a rare disease affects less than about 1 in 2,500 people.

In some embodiments, a rare disease affects less than about 1 in 1,500 people, 1 in 2,000 people, 1 in 2,500 people, 1 in 3,000 people, 1 in 4,000 people, 1 in 5,000 people, 1 in 6,000 people, 1 in 7,000 people, 1 in 8,000 people, 1 in 9,000 people, 1 in 10,000 people, 1 in 15,000 people, 1 in 20,000 people, 1 in 25,000 people, 1 in 30,000 people, 1 in 35,000 people, 1 in 40,000 people, 1 in 45,000 people, 1 in 50,000 people, 1 in 60,000 people, 1 in 70,000 people, 1 in 80,000 people, 1 in 90,000 people, 1 in 100,000 people, 1 in 150,000 people, or 1 in 200,000 people.

In some embodiments, the rare disease is a genetic disease. In some embodiments, the rare disease is monogenic. As used herein, "monogenic" means a disease caused by one or more mutations in a single gene. In some embodiments, the rare disease is autosomal recessive. In some embodiments, the rare disease is autosomal dominant. In some embodiments, the rare disease is sex-linked recessive (e.g., X-linked recessive). In some embodiments, the rare disease is sex-linked dominant.

In some embodiments, the rare disease is muscular dystrophy. In some embodiments, the rare disease is congenital muscular dystrophy (CMD). In some embodiments, the rare disease is Limb-girdle muscular dystrophy (LGMD). In some embodiments, the rare disease is caused by a deficient in any of the following genes: POMT1, POMT2, POMGNT1, LARGE, FKTN, and/or FKRP. In some embodiments, the optically visible phenotype for muscular dystrophy is decreased laminin binding.

Patients

In some embodiments, the rare disease presents in an adult. In some embodiments, the rare disease presents in a child.

The rare disease may have gradations of severity between individuals affected with the rare disease. For example, the rare disease may have gradations from undetectable to severely debilitating. The severity of the rare disease may depend on the number and type of genetic mutations. Drugs and nutraceuticals identified by the methods and platforms disclosed herein may be used to treat any gradations of the rare disease. Drugs and nutraceuticals identified by the methods and platforms disclosed herein may be used to prevent the development of symptoms of the rare disease.

Symptomatic Patients

In some embodiments, the patient is symptomatic, e.g., the patient has one or more symptoms of the rare disease. Medical professionals are aware of the symptoms of rare diseases. For example, the symptoms of Bechet's Disease include oral mucocutaneous ulcerations, genital ulcerations, erythema nodosum, cutaneous pustular vasculitis, educed visual acuity, reduced color vision, relative afferent pupillary defect, central scotoma, swollen optic disc, macular edema, and/or retrobulbar pain.

Grey Patients

In some embodiments, the patient presents with limited symptoms. In some embodiments, the patient is asymptomatic, e.g., the patient does not present with any symptoms. In some embodiments, patients with limited or no symptoms ("grey patients") are identified by genotyping. For example, one child in a family presents with a muscular dystrophy. The sibling does not display symptoms of a muscular dystrophy. A genotype screen is performed on the sibling and the sibling is identified as having genetic mutations that may result in development of a muscular dystrophy. The sibling is selected as a "grey" patient and a method or platform disclosed herein is used to identify and optimize a prophylactic treatment protocol for the sibling.

Exemplary Rare Diseases

Rare diseases include, but are not limited to, certain cancers, muscular dystrophies, laminopathies, diseases classified as part of the Finnish Disease Heritage. Non-limiting examples of rare diseases include Duchenne muscular dystrophy, congenital defects glycosylation (or, congenital disorder of glycosylation), Batten disease, multiple hereditary exostoses, Frank-ter Haar syndrome, familial dilated cardiomyopathy, MODY1 (or, maturity onset diabetes of the young 1), bipolar disorder, cystic fibrosis, aspartylglucosaminuria (or, AGU), infantile neuronal ceroid lipofuscinosisor (or, INCL), Salla disease, diastrophic growth disorder, cartilage-hair hypoplasia, Mulibrey disorder, retinoschisis, Usher syndrome, nonketotic hyperglycinemia, rapadilino, phenylketonuria (PKU), acid maltase deficiency (or, Pompe's disease), alkaptonuria (or, AKU), Alagille syndrome (or. AGS), alpha-1-antitrypsin deficiency (or, Alpha 1), Alport syndrome, ALS, Behcet's disease, porphyria, syringomyelia, Chiari malformation, amyloidosis, aplastic anemia, frontotemporal degeneration, glycogen storage disease, benign essential blepharospasm, cardiofaciocutaneous syndrome, carcinoid cancer, pancreatic neuroendocrine tumors, pheochromocytoma, Charcot-Marie-Tooth, spinal muscular atrophy (SMA), ataxia telangiectasia, Apert syndrome, Carpenter syndrome, cleft lip and/or palate, craniosynostosis, Crouzon syndrome, facial cleft, facial palsy, fibrous dysplasia, frontonasal dysplasia, hemangioma, hemifacial microsomia (Goldenhar syndrome), microtia/artresia, Miller syndrome, Moebuis syndrome, Nager syndrome, Pfeiffer syndrome, Pierre Robin sequence, Saethre-Chotzen, Treacher Collins, 18p-, distal 18q-, proximal 18q-, ring 18, tetrasomy 18p, trisomy 18, Pitt Hopkins syndrome, chronic granulomatous disease, cicatricial alopecia, Van Lohuizen syndrome (or, Cutis Marmorata Telangiectatica Congenita), pulmonary fibrosis, congenital hyperinsulinism, multiple sclerosis, Cornelia de Lange syndrome, progressive supranuclear palsy (PSP), Corticobasal degneration (CBD), Shy-Drager syndrome (or, multiple system atrophy (MSA) with postural hypotension), Cushing, Cutis laxa, cystinosis, desmoid tumors, Dravet, dysautonomia, dystonia, dystrophic epidermolysis bullosa, Erdheim-Chester disease (ECD), Ehlers-Danlos, erythromelalgia, fibromuscular dysplasia, fibrous dysplasia, ichthyosis, Freeman-Sheldon syndrome, Guillain-Barre syndrome, chronic inflammatory demyelinating polyneuropathy (CIDP), hemophilia, hereditary hemorrhagic telangiectasia (HHT), histiocytosis, hypothalamic harmartomas, Huntington's disease, hydrocephalus, incontinentia pigmenti, fibrodysplasia ossificans progressiva (FOP), CDKL5, Rett syndrome, intractable childhood epilepsy, Lennox-Gastaut syndrome, West syndrome, Dravet syndrome, Kennedy's disease, Klippel-Trenaunay, Lowe syndrome, lymphangioleiomyomatosis (LAM), mastocytosis, melorheostosis, myelofibrosis, essential thrombocythemia, polycythemia vera (PV), mucolipidosis type IV (ML4), Moebius syndrome, myasthenia gravis, myositis, narcolepsy, eosinophilia myalgia syndrome, ectodermal dysplasia, Fragile X, lymphedema, Marfan syndrome, Hurler-Scheie syndrome (MPS I), Hunter syndrome (MPS II), Sanfilippo syndrome (MPS III), Morquio syndrome (MPS IV), Maroteaux-Lamy syndrome (MPS VI), Sly syndrome (MPS VII), I-Cell disease (ML II), Pseudo-Hurler polydystrophy (ML III), multiple sclerosis, Niemann-Pick disease, spasmodic dysphonia, spasmodic torticollis, Tay-Sachs, tuberous sclerosis, neurofibromatosis, osteogenesis imperfect, oxalosis, hyperoxaluria, Paget's disease, Parkinson's disease, Phelan-McDermid syndrome, pseudomyxoma peritonei (PMP), Prader-Willi syndrome, primary sclerosing cholangitis, recurrent respiratory papillomatosis, reflex sympathetic dystrophy syndrome, scleroderma, Shwachman-Diamond syndrome, Sotos syndrome, Stevens Johnson syndrome, Sturge-Weber, Tourette syndrome, leukodystrophy, angioedema, vasculitis, Williams syndrome, Wilson's disease, Fukuyama congenital muscular dystrophy(FCMD), congenital muscular dystrophy unrelated to FCMD, Becker's muscular dystrophy, distal muscular dystrophy, Emery-Dreifuss muscular dystrophy, facioscapulohumeral muscular dystrophy, Limb-girdle muscular dystrophy, myotonic muscular dystrophy, or oculopharyngeal muscular dystrophy.

In some embodiments, the rare disease is associated with one or more biomarkers. In some embodiments, the biomarker is present in blood, plasma, or cell culture medium. In some embodiments, a biomarker associated with a rare disease is used to determine if a treatment for a rare disease (e.g., a treatment identified by the methods and platforms disclosed herein) is successful. In some embodiments, a biomarker associated with a rare disease is used to determine the systemic effects of a treatment for a rare disease (e.g., a treatment identified by the methods and platforms disclosed herein). In some embodiments, a biomarker associated with a rare disease is used to determine the dose response of a treatment for a rare disease (e.g., a treatment identified by the methods and platforms disclosed herein).

Optically-Visible Phenotypes

Disclosed herein, in certain embodiments, are methods of identifying a drug or nutraceutical candidate for normalizing, or partially normalizing, a rare-disease in a subject in need thereof. Further disclosed herein, in certain embodiments, are rare disease theranostics platforms. In some embodiments, the rare is associated with one or more optically visible cell phenotypes. In some embodiments, the methods and platforms further comprise identifying an optically-visible cell phenotype associated with a rare disease.

As used herein, "phenotype" means the observable characteristics or traits of a rare disease cell, e.g., its morphology, development, biochemical or physiological properties, phenology, behavior.

In some embodiments, the optically-visible rare-disease cell phenotype is selected from cell morphology, nuclear morphology (e.g., chromosomal morphology), morphology of the plasma membrane (e.g., the phospholipid bilayer, channels [e.g., ion channels, receptors], the morphology of any cytosolic organelle [e.g., the rough endoplasmic reticulum (ER), the smooth endoplasmic reticulum, ribosomes, the cytoskeleton (e.g. microfilaments, intermediate filaments and microtubules), the Golgi apparatus, mitochondria, vesicles, lysosomes, peroxisomes, centrosomes, centrioles, vacuoles). In some embodiments, the rare-disease cell phenotype is rendered optically-visible due to the use of an optically-visible dye/label.

In some embodiments, the optically-visible rare-disease cell phenotype is abnormal laminin binding, or abnormal lamin A/C or lamin B binding.

Laminins

Laminins are components of the basal lamina. Laminins influence cell differentiation, migration, and adhesion, as well as phenotype and survival. Laminins are trimeric proteins that intersect to form a cross-like structure that binds to other cell membrane and extracellular matrix molecules. The three shorter arms are particularly good at binding to other laminin molecules, which allows them to form sheets. The long arm is capable of binding to cells, which helps anchor organized tissue cells to the membrane. Laminins are an integral part of the structural scaffolding in almost every tissue of an organism. They are secreted and incorporated into cell-associated extracellular matrices. Laminin is vital for the maintenance and survival of tissues. Defective laminins can cause muscles to form improperly, leading to muscular dystrophies.

Lamins

Nuclear lamins, also known as Class V intermediate filaments, are fibrous proteins providing structural function and transcriptional regulation in the cell nucleus. Nuclear lamins interact with membrane-associated proteins to form the nuclear lamina on the interior of the nuclear envelope They attach to the nuclear envelope membrane via farnesyl anchors and interaction with inner nuclear membrane proteins such as lamin B receptor. Defects in lamins result in abnormal lamin binding, for example abnormal lamin binding to the nuclear envelope. Abnormal lamin binding is associated with nuclear envelope instability in physically stressed tissues such as muscle fibers, bone, skin and connective tissue.

Dyes/Labels

In some embodiments, the optically-visible rare-disease cell phenotype comprises an optically-visible label. In some embodiments, the rare-disease cell phenotype is rendered optically-visible due to the use of an optically-visible label. As used herein, the term "optically visible label" refers to a molecule that facilitates the visualization and/or detection of a targeting molecule disclosed herein. The optically visible label may be directly observable by the eye (e.g., the optically visible label is a fluorescent dye) or it may be visible due to interaction with an intermediate device (e.g., the optically visible label is a radioactive label that is visible following exposure of film or by use of a use of a gamma scintillation camera).

In some embodiments, the optically visible label directly binds (e.g., dyes) a rare disease cell or one or more components of the cell (e.g., the nucleus, or an organelle, a protein, a lipid, or a polysaccharide).

In some embodiments, the optically visible label indirectly binds a rare disease cell or one or more components of the cell (e.g., the nucleus, or an organelle, a protein, a lipid, or a polysaccharide). For example, in some embodiments, the optically visible label is bound to an antibody that binds to a rare disease cell or one or more components of the cell (e.g., the nucleus, or an organelle, a protein, a lipid, or a polysaccharide). In some embodiments, the optically visible label is bound to streptavidin (or avidin) which is bound to biotin, the biotin being bound to an antibody that binds to a rare disease cell or one or more components of the cell (e.g., the nucleus, or an organelle, a protein, a lipid, or a polysaccharide).

In some embodiments, the optically visible label is a dye. In some embodiments, the optically visible label is a fluorescent moiety. In some embodiments, the fluorescent moiety is selected from: a fluorescent protein, a fluorescent peptide, a fluorescent dye, a fluorescent material or a combination thereof.

All fluorescent moieties are encompassed within the term "fluorescent moiety." Specific examples of fluorescent moieties given herein are illustrative and are not meant to limit the fluorescent moieties for use with the targeting molecules disclosed herein.

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzo furans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes.

Examples of fluorescein dyes include, but are not limited to, 5-carboxyfluorescein, fluorescein-5-isothiocyanate, fluorescein-6-isothiocyanate and 6-carboxyfluorescein.

Examples of rhodamine dyes include, but are not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®).

Examples of cyanine dyes include, but are not limited to, Cy3, Cy3B, Cy3.5, Cy5, Cy5.5, Cy7, IRDYE680, Alexa Fluor 750, IR800CW, ICG.

Examples of fluorescent peptides include GFP (Green Fluorescent Protein) or derivatives of GFP (e.g., EBFP, EBFP2, Azurite, mKalamal, ECFP, Cerulean, CyPet, YFP, Citrine, Venus, YPet).

Fluorescent labels are detected by any suitable method. For example, a fluorescent label may be detected by exciting the fluorochrome with the appropriate wavelength of light and detecting the resulting fluorescence, e.g., by microscopy, visual inspection, via photographic film, by the use of electronic detectors such as charge coupled devices (CCDs), photomultipliers, etc.

In some embodiments, the optically-visible label is a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound.

In some embodiments, the optically-visible label is a nuclear probe. In some embodiments, the imaging agent is a SPECT or PET radionuclide probe. In some embodiments, the radionuclide probe is selected from: a technetium chelate, a copper chelate, a radioactive fluorine, a radioactive iodine, a indiuim chelate.

Examples of Tc chelates include, but are not limited to HYNIC, DTPA, and DOTA.

In some embodiments, the optically-visible label is a radioactive moiety, for example a radioactive isotope such as $^{211}$At, $^{131}$I, $^{125}$I, $^{90}$Y, $^{186}$Re, $^{188}$Re, $^{153}$Sm, $^{212}$Bi, $^{32}$P, $^{64}$Cu radioactive isotopes of Lu, and others.

In some embodiments, the optically-visible label is a positron-emitting isotope (e.g., $^{18}$F) for positron emission tomography (PET), gamma-ray isotope (e.g., $^{99m}$Tc) for single photon emission computed tomography (SPECT), or a paramagnetic molecule or nanoparticle (e.g., $Gd^{3+}$ chelate or coated magnetite nanoparticle) for magnetic resonance imaging (MRI).

In some embodiments, the optically-visible label is a gadolinium chelate, an iron oxide particle, a super paramagnetic iron oxide particle, an ultra small paramagnetic particle, a manganese chelate or gallium containing agent.

Examples of gadolinium chelates include, but are not limited to diethylene triamine pentaacetic acid (DTPA), 1,4,7,10-tetraazacyclododecane-1,4,7,10-tetraacetic acid (DOTA), and 1,4,7-triazacyclononane-N,N',N"-triacetic acid (NOTA).

Genotyping

Disclosed herein, in certain embodiments, are methods of identifying a drug or nutraceutical candidate for normalizing, or partially normalizing, an optically-visible rare-disease cell phenotype in a subject in need thereof. Further disclosed herein, in certain embodiments, are rare disease theranostics platforms. In some embodiments, the methods and platforms comprise genotyping an individual.

In some embodiments, the individual presents with a rare disease. In some embodiments, the individual is genotyped to determine which strain of the rare disease the individual has. In some embodiments, the individual presents with symptoms of multiple diseases (e.g., muscle aches) and the individual is genotyped to determine what disease (e.g., what rare disease) the individual has.

In some embodiments, the individual is a grey patient (i.e., the individual presents limited or no symptoms). In some embodiments, the individual presents with no symptoms and is genotyped to determine if he or she is predisposed to develop a rare disease. For example, the individual is genotyped as part of a yearly physical or the individual has a relative with a rare disease and is genotyped as a precaution. In some embodiments, the individual presents with limited symptoms and is genotyped to determine if he or she has a rare disease.

Any suitable method is used to genotype a patient. Suitable methods of sequencing DNA for use with the methods and platforms disclosed herein include, but are not limited to, restriction fragment length polymorphism identification (RFLPI) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads.

Assay

Disclosed herein, in certain embodiments, are methods of identifying a drug or nutraceutical candidate for normalizing, or partially normalizing, an optically-visible rare-disease cell phenotype in a subject in need thereof, comprising (a) contacting a plurality of cells having the optically-visible rare-disease cell phenotype with a drug or nutraceutical from a drug/nutraceutical library, (b) obtaining a magnified image of the plurality of cells following contact with the drug or nutraceutical from the drug/nutraceutical library; and (c) analyzing the magnified images to determine the response of the plurality of cells to the drug or nutraceutical from the drug/nutraceutical library. Further disclosed herein, in certain embodiments, are rare disease theranostics platforms, comprising: (a) a cell-phenotype image-enhancing instrument; (b) a drug/nutraceutical library; and (c) a computer-implemented system for analyzing a response of an optically-visible rare-disease cell phenotype to a drug or nutraceutical from the drug/nutraceutical library.

In some embodiments, a cell having an optically-visible rare disease cell phenotype is contacted with a drug or nutraceutical from a drug/nutraceutical library. In some embodiments, the cell is incubated with the drug/nutraceutical for a period of time sufficient to normalize or partially normalize the optically-visible rare disease phenotype.

Visualization/Microscopy

In some embodiments, the results of incubating a cell having an optically-visible rare disease cell phenotype with a drug or nutraceutical are visualized. In some embodiments, the results of the incubation are manually visualized. In some embodiments, the results of the incubation are visualized with a cell-phenotype image-enhancing instrument. In some embodiments, the results of the incubation are visualized with an automated cell-phenotype image-enhancing instrument. In some embodiments, the cell-phenotype image-enhancing instrument is any instrument (e.g., an automated instrument) that is suitable for visualizing an optically-visible rare disease cell phenotype.

In some embodiments, the cell-phenotype image-enhancing instrument comprises a microscope (e.g., an automated microscope). In some embodiments, the cell-phenotype image-enhancing instrument comprises: (a) a detector for imaging the optically-visible rare-disease cell phenotype; (b) magnification optics having sufficient magnifying power to visualize one cell in a plurality of cells; and (c) an available electronic memory for storing an image of a cell. In some embodiments, the phenotype image-enhancing instrument comprises sufficient optics to visualize one organelle in a cell. In some embodiments, a microscope for use with the methods and platforms disclosed herein has at least a resolution of between 1 nm and 600 nm, for example between 1 nm and 200 nm, between 1 nm and 100 nm, between 1 nm and 50 nm, between 1 nm and 20 nm, and between 1 nm and 10 nm.

In some embodiments, the cell-phenotype image-enhancing instrument comprises a fluorescence microscope (e.g., an automated fluorescence microscope). In some embodiments, the cell-phenotype image-enhancing instrument comprises an electron microscope (e.g., an automated electron microscope).

High Content Screening

In some embodiments, the assays and methods disclosed herein are conducted by High Content Screening (HCS). In some embodiments, use of HCS allows for the rapid identification of drugs and/or nutraceuticals that normalize, or partially normalize, an optically-visible rare-disease cell phenotype in a subject in need thereof.

High Content Screening comprises microscopy (e.g., fluorescence microscopy) to image cells with an optically visible rare disease cell phenotype and image analysis to measure changes in the properties of the cells (e.g., normalization or partial normalization) caused by contact with a known drug (e.g., a drug approved for use by the US FDA, a drug whose use predates the establishment of the FDA, a drug approved for use ex-US, or a drug that has entered or completed phase II trials), a metabolite of a known drug, or a nutraceutical.

In some embodiments, the HCS system comprises a microscope (e.g., a fluorescence microscope) and electronic memory for storing an image of a cell. In some embodiments, the HCS system further comprises automated liquid handling, automated plate handling, image analysis software, or any combination thereof.

In some embodiments, the HCS system comprises a confocal microscope. In some embodiments, the HCS system comprises a widefield microscope. In some embodiments, the HCS system is a live cell temperature controlled imaging system. In some embodiments, the HCS system is ImageXpress ULTRA (Molecular Devices), Pathway 855 and 435 (Becton Dickinson Biosciences), Opera (PerkinElmer Inc.), IN Cell 3000 (GE/Amersham Biosciences), Arrayscan VTI (Cellomics), IN Cell Analyzer 2000 (GE Healthcare), Acumen eX3 (TTP LabTech Ltd), Scanalyzer (Scanalyzer LemnaTec), or ImageXpress MICRO (Molecular Devices), IN Cell 1000 (GE/Amersham Biosciences), Pathway HT (Becton Dickinson Biosciences), or Cell Observer (Carl Zeiss).

In some embodiments, the HCS system further comprises automated liquid handling, e.g., Sciclone G3 Liquid Handling Workstation (PerkinElmer) or Zephyr Compact Liquid Handling (PerkinElmer). In some embodiments, the HCS system further comprises automated plate handling, e.g., Twister II Plate Handler (PerkinElmer).

In some embodiments, the HCS system further comprises computer software for image analysis. Examples of suitable image analysis software includes, but is not limited to, IN Cell Investigator (PerkinElmer), LemnaLauncher (LemnaTec), bioImageXD, CellProfiler, ImageJ, Pipeline Pilot (Accerlys).

In some embodiments, the cell-phenotype image-enhancing instrument is an Opera System (Perkin Elmer).

Image Analysis

In some embodiments, the response of the optically-visible rare-disease cell phenotype to a drug or nutraceutical from the drug/nutraceutical library is detected or visualized by the cell-phenotype image-enhancing instrument.

In some embodiments, a computer implemented system (e.g., computer software for image analysis) analyzes degrees of response of the optically-visible rare-disease cell phenotype to a drug or nutraceutical in the drug/nutraceutical library. In some embodiments, the computer implemented system comprises an algorithm that determines degrees of response of the optically-visible rare-disease cell phenotype to a drug or nutraceutical in the drug/nutraceutical library.

In some embodiments, the computer-implemented system outputs the results of the methods and platforms disclosed herein as a numeric value corresponding to a quantitative or qualitative value obtained from contacting a rare disease cell with a drug or nutraceutical. For example, where the rare disease cell phenotype is made optically visible by use of a fluorescent dye, the quantitative value may be the level of fluorescence of the dye. The quantitative value may also be, by way of non-limiting example, the number/presence of a selected organelle, nuclear size/dimension, cell size/dimension, cellular area, or nuclear area. The qualitative value may be, by way of non-limiting example, cellular shape or nuclear shape.

In some embodiments, the computer-implemented system compares the experimental results to a positive and/or negative control. In some embodiments, the computer-implemented system compensates for background noise (e.g., background fluorescence).

In some embodiments, the response of the optically-visible rare-disease cell phenotype to a drug or nutraceutical in the drug/nutraceutical library correlates with the effect of the drug or nutraceutical on at least one symptom of the rare disease in vivo.

In some embodiments, the methods and platforms disclosed herein identify at least one drug or nutraceutical from the library that normalizes or partially normalizes the optically-visible rare-disease cell phenotype (i.e., a "hit").

In some embodiments, date from the methods and platforms disclosed herein are used to identify dose-response curves for any drug and/or nutraceutical hits.

Follow-Up/Secondary Screen

In some embodiments, the methods disclosed herein further comprise a second (follow-up) screen utilizing any drugs and/or nutraceuticals that normalized or partially normalized an optically visible rare disease cell phenotype. In some embodiments, the second screen is used to eliminate false positive hits and hits with low effect. In some embodiments, the second screen optimizes the concentrations of any drug and/or nutraceutical hits, e.g., data from the second screen is used to identify dose-response curves for any drug and/or nutraceutical hits.

Drug Libraries

Disclosed herein, in certain embodiments, are methods of identifying a drug or nutraceutical candidate for normalizing, or partially normalizing, an optically-visible rare-disease cell phenotype in a subject in need thereof, comprising (a) contacting a plurality of cells having the optically-visible rare-disease cell phenotype with a drug or nutraceutical from a drug/nutraceutical library, (b) obtaining a magnified image of the plurality of cells following contact with the drug or nutraceutical from the drug/nutraceutical library; and (c) analyzing the magnified images to determine the response of the plurality of cells to the drug or nutraceutical from the drug/nutraceutical library. Further disclosed herein, in certain embodiments, are rare disease theranostics platforms, comprising: (a) a cell-phenotype image-enhancing instrument; (b) a drug/nutraceutical library; and (c) a computer-implemented system for analyzing a response of an optically-visible rare-disease cell phenotype to a drug or nutraceutical from the drug/nutraceutical library.

In some embodiments, the drug/nutraceutical libraries for use with the platforms and methods disclosed herein comprise known drugs, metabolites of known drugs, and/or nutraceuticals. In some embodiments, a drug/nutraceutical library for use with a method or platform disclosed herein comprises about 50, about 100, about 150, about 2000, about 250, about 300, about 350, about 400, about 450, about 500, about 550, about 600, about 650, about 700, about 750, about 800, about 850, about 900, about 950, about 1000, about 1250, about 1500, about 1750, about 2000, about 2500, about 3000, about 3500, about 4000, about 4500, about 5000, about 6000, about 7000, about 8000, about 9000, about 10000 known drugs, metabolites of known drugs, and/or nutraceuticals.

Known drugs for use with the platforms and methods disclosed herein include any drug that is currently being used for human or veterinary use, has been used for human or veterinary use, or has been studied by medical professionals in a clinical setting (e.g., a clinical trial, e.g., a phase I clinical trial, a phase II clinical trial, a phase III clinical trial, a phase IV clinical trial). Examples of known drugs for use with the platforms and methods disclosed herein include, but are not limited to, drugs approved by a national regulatory agency (e.g., the United States Federal Drug Administration (FDA), the European Medicines Agency, the UK Medicines and Healthcare Products Regulatory Agency, the Therapeutic Products Directorate (TPD) of Health Canada, the Australian Therapeutic Goods Administration, the Chinese State Food and Drug Administration, the Japanese Pharmaceuticals and Medical Devices Agency) as an over-the-counter medicine or a prescription medicine, drugs classified as GRAS/E (Generally Regarded as Safe and Effective) by the US FDA, drugs listed in the US FDA Orange Book, drugs listed in any edition of the Physicians' Desk Reference (PDR), drugs listed in any edition of the American Hospital Formulary Service Drug Information (AHFS DI), drugs listed in the Merck Index, or any combination thereof.

Known drugs for use with the methods and platforms disclosed herein include, but are not limited to, cancer drugs (see e.g., those listed by the National Cancer Institute), anti-inflammatory drugs (e.g., steroids, and non-steroidal anti-inflammatory drugs (NSAIDs)), antimicrobial drugs (e.g., antibacterials, antifungals, antivirals, antiparasitics (e.g., antiematodes, anticestodes, antirematodes, antiamoebics, antiprotozoals), antipyretics, analgesics, antiseptics, antiemetics, antinauseants, laxatives, antidiarrheals, digestives, orexigenics, diabetes drugs (e.g., insulins and analogues, blood glucose lowering drugs, except for insulins, aldose reductase inhibitors), antacids, H2-receptor antagonists, prostaglandins, proton pump inhibitors, anticholinergics, antispasmodics, antithrombotics, antihemorrhagics, antianemics, antihypertensives, diuretics, vasodilators, beta blocking agents, calcium channel blockers, ACE inhibitors, angiotensin II receptor antagonists, rennin inhibitors, antihyperlipidemics (e.g., statins, fibrates), hormones (e.g., sex hormones), immunostimulants, immunosuppressants, Decongestants, bronchodilators, cough medicines, H1 antagonists, analgesicsa, anesthetics (General, Local), anorectics, anti-aDHD agents, antiaddictives, anticonvulsants, antidementia agents, antidepressants, antimigraine agents, antiparkinson's agents, antipsychotics, anxiolytics, depressants, entactogens, entheogens, euphoriants, hallucinogens (psychedelics, Dissociatives, Deliriants), hypnotics/Sedatives, mood stabilizers, neuroprotectives, nootropics, neurotoxins, orexigenics, serenics, stimulants, antirheumatics, muscle relaxants, bisphonates.

Alternatively, known drugs for use with the methods and platforms disclosed herein includes those classified under ATC (Anatomical Therapeutic Chemical Classification System) code A (Alimentary tract and metabolism); B (Blood and blood forming organs); C (Cardiovascular system); D (Dermatologicals); G (Genito-urinary system and sex hormones); H (Systemic hormonal preparations, excluding sex hormones and insulins); J (Antiinfectives for systemic use); P (Antiparasitic products, insecticides and repellents); QI (Immunologicals); L (Antineoplastic and immunomodulating agents); M (Musculo-skeletal system); N (Nervous system); R (Respiratory system); S (Sensory organs); and V (Various).

Non-limiting examples of nutraceuticals for use with the platforms and methods disclosed herein include: vitamins, minerals, herbs or other botanicals (e.g., those used in traditional Chinese Medicine, e.g., ginger, garlic), amino acids, enzymes, metabolites, antioxidants (e.g., resveratrol; flavonoids; anthocyanins), isoflavanoids, organosulfur compounds (e.g., sulforaphane), omega 3 fatty acids (e.g., alpha-linolenic acid), and functional foods (i.e., enriched foods, e.g., milk supplemented with vitamin D).

Exemplary drug/nutraceutical libraries for use with the methods and platforms disclosed herein include the NINDS (National Institute of Neurological Disorders and Stroke) Custom Collection, the Biomol 3—ICCB Known Bioactives library, the Prestwick2 collection, the NIH Clinical Collection 1, the NIH Clinical Collection 2, the Sigma LOPAC 1 library, the Tocriscreen Mini Library, the EMD Kinase Inhibitor 1 library, the SYNthesis Kinase Inhibitor 1 library, the MSDiscovery 1 library, the Microsource 1—US Drug Collection, the ENZO Life Sciences' BML-2841 library (either the 100 ul or 500 ul/well libraries), DTP Approved Oncology Drugs Set III, DTP Diversity Set III, DTP Mechanistic Set, Natural Product Set II, MSDiscovery Pharmakon 1600, MSDiscovery Spectrum Collection, MSDiscovery US Drug Collection, MSDiscovery International Drug Collection, MSDiscovery Pure Natural Products, the Starr Foundation Extracts 2 library, the ATCHEC I-1 library, the ATCHEC I-2 library, the ATCHEC I-3 library, the ATCHEC II-1 library, the ATCHEC II-2 library, and the ATCHEC II-3 library.

TABLE 1

| Library Name | Number of Compounds |
| --- | --- |
| NINDS Custom Collection 2 | 1,040 |
| Biomol 3 - ICCB Known Bioactives - High Conc. | 480 |
| Prestwick2 Collection | 1,120 |
| NIH Clinical Collection 1 | 450 |
| NIH Clinical Collection 2 | 312 |
| Sigma LOPAC (Library of Pharmacologically Active Compounds) 1 | 1280 |
| Tocriscreen Mini Library | 1,120 |
| EMD Kinase Inhibitor 1 | 244 |
| SYNthesis Kinase Inhibitor 1 | 96 (x3) |
| Microsource 1 - US Drug Collection | 1,040 |
| Enzo Life Sciences - ICCB Known Bioactives Library (BML-2841; formerly, Biomol 4 - FDA Approved Library) | 640 |
| DTP Approved Oncology Drugs Set III | 97 |
| DTP Diversity Set III | 1597 |
| DTP Mechanistic Set | 879 |
| Natural Product Set II | 120 |
| MSDiscovery Pharmakon 1600 | 1600 |
| MSDiscovery Spectrum Collection | 2000 |
| MSDiscovery US Drug Collection | 1280 |
| MSDiscovery International Drug Collection | 320 |
| MSDiscovery Pure Natural Products | 800 |
| Johns Hopkins Clinical Compound library | 3,100 |

Currently available drug/nutraceutical libraries for use with the methods and platforms disclosed herein include compounds selected from the following: (+)-cis-diltiazem hydrochloride; (+)naproxen; (+/−)-epinephrine hydrochloride; (+/−)-norepinephrine hydrochloride; (−)-menthol; -d-arabinofuranoside; 1,2-dimethylhydrazine hydrochloride; 1,3-dipropyl-8-cyclopentylxanthine [dpcpx]; 1-phenylbiguanide hydrochloride; 1r,9s-hydrastine; 1s,2r-phenylpropanolamine hydrochloride; 1s,9r-beta-hydrastine; 1s-camphor; 2,3-dihydroxy-6,7-dichloroquinoxaline; 2,6-di-t-butyl-4-methylphenol; 2-mercaptobenzothiazole; 3,5,3'-triiodothyronine; 3,5-dinitrocatechol (OR-486); 3-aminobenzamide; 3-aminopropanesulphonic acid; 3-methyl-1-phenyl-2-pyrazolin-5-one (MCI-186); 4-(aminomethyl)benzenesulfonamide acetate; 5-azacytidine; 5-fluorouracil; 5-nitro-2-phenylpropylaminobenzoic acid [NPPB]; 6-[2-ethoxy-1-naphthamido]-penicillin sodium salt; 6alpha-methyl-11beta-hydroxyprogesterone; 7,8-dihydroxyflavone; 7-hydroxyethyltheophylline; 8-cyclopentyltheophylline; 9-amino-1,2,3,4-tetrahydroacridine hydrochloride; 17-beta-estradiol 17-valerate; 18alpha-glycyrrhetinic acid; 19-norethindrone; 19-norethindrone acetate; acacetin; acebutolol hydrochloride; aceclidine hydrochloride; acemetacin; acetaminophen; acetaminosalol; acetanilide; acetarsol; acetazolamide; acetohydroxamic acid; acetriazoic acid; acetyl-1-leucine; acetylcarnitine; acetylcholine; acetylcysteine; acetylglucosamine; acetylglutamic acid; acetylphenylalanine; acetylserotonin; acetyltryptophan; acetyl tyrosine ethyl ester; acexamic acid; acitretin; acivicin; aclacinomycin a1; aconitine; acrichine; acriflavinium hydrochloride; acrisorcin; actinonin; acyclovir; adenine 9-beta; adenosine; adenosine phosphate; adrenaline bitartrate; aesculin; ajmaline; aklavine hydrochloride; alanyl-dl-leucine; alanyl-dl-phenylalanine; alaproclate; albalon; albendazole; albuterol; alexidine hydrochloride; allantoin; allegra; allopurinol; allopurinol; almotriptan; aloin; alpha-cyano-3-hydroxycinnamic acid; alpha-cyano-4-hydroxycinnamic acid; alpha-tochopherol; alpha-tochopheryl acetate; alprenolol; altretamine; altretamine; alverine citrate; amantadine hydrochloride; ambroxol hydrochloride; amcinonide; amifostine; amikacin sulfate; amiloride hydrochloride; aminocaproic acid; aminoglutethimide; aminohippuric acid; aminohydroxybutyric acid; aminolevulinic acid; aminolevulinic acid; aminolevulinic acid hydrochloride; aminophenazone; aminopyridine; aminothiazole; amiodarone hydrochloride; amiprilose; amitriptyline hydrochloride; amlodipine besylate; amodiaquine dihydrochloride; amoxapine; amoxepine; amoxicillin; amoxicillin crystalline; ampicillin sodium; amprolium; aminone; amygdalin; anabasamine hydrochloride; anabasine hydrochloride; anafranil; anastrozole; ancitabine hydrochloride; androsterone sodium sulfate; aniracetam; anisindione; anisodamine; anisomycin; annoyltin; antazoline phosphate; anthralin; antimycin a; antipyrine; aphyllic acid; apomorphine hydrochloride; arachidonic acid; arcaine sulfate; arecoline hydrobromide; arsenic trioxide; artane; artemisinin; asarinin (−); aspirin; atenolol; atractyloside potassium; atropine; aureomycin; austricine; avermectin b1; azacitidine; azadirachtin; azaserine; azathioprine; azelaic acid; azithromycin; azlocillin sodium; azobenzene; bacampicillin hydrochloride; bacitracin; baclofen; baicalein; batyl alcohol; becanamycin sulfate; beclomethasone dipropionate; benazepril hydrochloride; bendamustine HCl; bendrofluazide; bendrofumethiazide; benfluorex hydrochloride; benfotiamine; benserazide hydrochloride; bentyl; benzalkonium chloride; benzenebutanoic acid; benzethonium chloride; benzocaine; benzthiazide; benztropine; benzyl benzoate; berberine chloride; bergapten; beta-carotene; beta-escin; beta-peltatin; betahistine hydrochloride; betaine hydrochloride; betamethasone; betamethasone 17,21-dipropionate; betamipron; bethanechol chloride; betulinic acid; bezafibrate; bicuculline (+); biochanin a; biotin; bisacodyl; bithionol; bleomycin; bleomycin (bleomycin b2 shown); bortezomib; bretylium tosylate; brimonidine; bromhexine hydrochloride; bromocriptine mesylate; bromopride; broxyquinoline; bucladesine; budesonide; bumetanide; bupivacaine hydrochloride; bupropion; buspar; busulfan; busulfan; butacaine; butamben; butirosin sulfate; cabazitaxel; cacodylic acid; caffeine; calcein; camptothecin; canavanine; cantil; capecitabine; capreomycin sulfate; captopril; carbachol; carbamazepine; carbenicillin disodium; carbenoxolone sodium; carbetapentane; carbidopa; carbinoxamine maleate; carboplatin; carboplatin; cardene; carisoprodol; carmustine; carmustine; carnitine hydrochloride; carvedilol; cefadroxil; cefamandole sodium; cefazolin sodium; cefazolin sodium salt; cefdinir; cefmetazole sodium; cefoperazone sodium; cefotaxime sodium; cefotaxime sodium salt; cefoxitin sodium; cefoxitin sodium salt; cefsulodin sodium; ceftibuten; ceftriaxone sodium; cefuroxime; cefuroxime sodium; celastrol; celecoxib; celecoxib; cephaloridine; cephalosporin c sodium; cephalothin sodium; cephapirin sodium; cephradine; cetirizine; cetrimonium bromide; cetylpyridinium chloride; chaulmoogric acid, ethyl ester; chenodiol; chlorambucil; chlorambucil; chloramphenicol; chloramphenicolhemisuccinate; chlordiazepoxide; chlorguanide hydrochloride; chlorhexidine; chloroacetoxyquinoline; chlorocresol; chloroquine diphosphate; chlorothiazide; chlorotrianisene; chloroxine; chloroxylenol; chlorpheniramine (s) maleate; chlorpromazine; chlorpropamide; chlorprothixene hydrochloride; chlorthalidone; chlorzoxazone; choline chloride; chromocarb; chrysin; cianidanol; ciclopirox olamine; cimetidine; cinchonidine; cinchonine; cinnarazine; cinoxacin; ciprofloxacin; cisplatin; cisplatin; citalopram; citiolone; citrinin; citropten; cladribine; clarithromycin; clenbuterol hydrochloride; clidinium bromide; clindamycin hydrochloride; clobetasol propionate; clofarabine; clofibrate; clofibric acid; clofoctol; clomid; clomiphene citrate; clomipramine hydrochloride; clonidine hydrochloride; clopamide; cloperastine hydrochloride; clopidogrel; clopidogrel sulfate; clotrimazole; cloxacillin sodium; cloxyquin; clozapine; cobalamine; coenzyme q10; cogentin mesylate; colchiceine; colchicine; colforsin; colistimethate sodium; compactin; cortell; cortisone acetate; cotinine; creatinine; cresol; crizotinib; cromolyn sodium; crustecdysone; cyclobenzaprine hydrochloride; cyclocreatine; cycloheximide; cyclo leucine; cycloleucylglycine; cyclopentolate hydrochloride; cyclophosphamide; cyclophosphamide hydrate; cyclopiazonic acid; cycloserine; cyclosporine; cyclothiazide; cypermethrin; cyproterone; cyproterone acetate; cystamine dihydrochloride; cytarabine; cytarabine HCl; cytisine; cytoxan; d-cycloserine; d-phenylalanine; dacarbazine; dacarbazine; dactinomycin; daidzein; danazol; dantrolene sodium; dantrolene sodium salt; dantron; dapsone; dasatinib; daunorubicin HCl; daunorubicin hydrochloride; decitabine; deet; deferoxamine mesylate; deltaline; demeclocycline; demeclocycline hydrochloride; depo-medrol; deprenalin; dequalinium chloride; desipramine hydrochloride; desoxycorticosterone acetate; dexamethasone; dexamethasone acetate; dexamethasone sodium phosphate; dexrazoxone; dextromethorphan hydrobromide; diazepam; dibekacin; dibenzothiophene; dibenzyline; dibucaine hydrochloride; dichlorophene; diclofenac sodium; dicloxacillin sodium; dicumarol; dicyclomine hydrochloride; dieldrin; dienestrol; diethylcarbamazine citrate; diethylstilbestrol; diffratic acid; diflucortolone pivalate; diflunisal; digitoxin; digoxin; dihydroartemisinin; dihydrosamidin; dihydrostreptomycin sulfate; dilantin; dimenhydrinate; dimercaptopropanol; dimethadione; dinitolmide; diosmin; dioxybenzone; diphenhydramine hydrochloride; diphenylpyraline hydrochloride; diplosalsalate; diprotin a; dipyridamole; dipyrocetyl; dipyrone; dirithromycin; disipal; disopyramide phosphate; dl-penicillamine; dobutamine hydrochloride; docetaxel; donepizil hydrochloride; dopamine hydrochloride; doxazosin; doxepin hydrochloride; doxorubicin HCl; doxycycline; doxycycline hydrochloride; doxylamine succinate; drofenine hydrochloride; droperidol; dropropizine; duremesin; duvadilan; dyclonine hydrochloride; dyphylline; e-capsaicin; ebselen; eburnamonine; econazole nitrate; edoxudine; edrophonium chloride; ellagic acid; emetine; emodic acid; enalapril maleate; enoxacin; enoxolone; ephedrine (1r,2s) hydrochloride; equilin; ergocalciferol; erlotinib HCl; eryped; erythromycin; erythromycin estolate; erythromycin ethylsuccinate; estradiol; estradiol-3-sulfate, sodium salt; estradiol cypionate; estradiol propionate; estradiol valerate; estramustine disodium phosphate; estriol; estriol benzyl ether; estrone; estrone acetate; estrone hemisuccinate; eszopiclone; etanidazole; ethacrynic acid; ethambutol; ethambutol hydrochloride; ethaverine hydrochloride; ethinyl estradiol; ethionamide; ethisterone; ethopropazine hydrochloride; ethosuximide; ethoxyquin; ethyl 1-benzyl-3-hydroxy-2-oxo[5h]pyrrole-4-carboxylate; ethyl-norepinephrine hydrochloride; etodolac; etomidate; etoposide; eucatropine hydrochloride; eugenol; everolimus; evista; exalamide; exemestane; ezetimibe; famciclovir; famotidine; felamidin; felodipine; fenbendazole; fenbufen; fenbutyramide; fendiline hydrochloride; fenofibrate; fenoprofen; fenoterol hydrobromide; fenspiride hydrochloride; fexofenadine hydrochloride; fipexide hydrochloride; flecamide acetate; flopropione; floxuridine; floxuridine; fluconazole; fludarabine; fludarabine; fludrocortisone acetate; flufenamic acid; flufenazine hydrochloride; flumadine; flumequine; flumethasone; flumethazone pivalate; flunarizine hydrochloride; flunisolide; fluocinolone acetonide; fluocinolone acetonide 21-acetate; fluocinonide; fluorometholone; fluorouracil; fluorouracil; fluoxetine; flurandrenolide; flurbiprofen; flutamide; flutrimazole; fluvastatin; folic acid; formestane; foscarnet sodium; fosfosal; fosphomycin; fulvestrant; furazolidone; furosemide; fusidic acid; gaboxadol hydrochloride; galanthamine hydrobromide; gallamine; gambogic acid; gamma-aminobutyric acid; ganciclovir; gatifloxacin; gedunin; gefitinib; geldanamycin; gemcitabine HCl; gemfibrozil; gentamicin sulfate; gentian violet; gentisic acid; glafenine; gliclazide; glipizide; gluconolactone; glucosamine hydrochloride; glutathione; glyburide; glycopyrrolate; gossypol-acetic acid complex; griseofulvin; guaiazulene; guaifenesin; guanabenz acetate; guanethidine sulfate; halazone; halcinonide; haloperidol; harmaline; harmalol hydrochloride; harmol hydrochloride; hecogenin; helenine; heptaminol hydrochloride; hesperetin; hesperidin; hetacillin potassium; hexachlorophene; hexamethonium bromide; hexestrol; hexetidine; hexylresorcinol; hieracin; histamine dihydrochloride; homatropine bromide; homatropine methylbromide; homidium bromide; hycanthone; hydralazine hydrochloride; hydrastinine hydrochloride; hydrochlorothiazide; hydrocortisone; hydrocortisone acetate; hydrocortisone butyrate; hydrocortisone hemisuccinate; hydrocortisone sodium phosphate; hydroflumethiazide; hydroquinidine; hydroquinone; hydroxyprogesterone caproate; hydroxytacrine maleate; hydroxyurea; hydroxyurea; hydroxyzine pamoate; hyoscyamine; ibuprofen; ifosfamide; imatinib; imipramine hydrochloride; imiquimod; imodium; indapamide; inderal; indomethacin; indoprofen; intropin; iodoquinol; iopanic acid; ipratropium bromide; ipratropium bromide monohydrate; ipriflavone; iproniazid sulfate; irinotecan HCl; isoliquiritigenin; isoniazid; isopilocarpine nitrate; isopropamide iodide; isoproterenol hydrochloride; isoreserpine; isosorbide dinitrate; isotretinoin; isoxicam; isoxsuprine hydrochloride; isuprel; ixabepilone; juglone; kanamycin sulfate; katacine; kemadrin; ketoconazole; ketoprofen; ketorolac tromethamine; ketotifen fumarate; khellin; kinetin; kojic acid; kynurenic acid; l-thyroxine; labetalol hydrochloride; lactulose; lamivudine; lanatoside c; lansoprazole; lapatinib; lasalocid sodium; lefunamide; lenalidomide; letrozole; leucine enkephalin; leucodin; leucovorin calcium; levamisole hydrochloride; levodopa; levonordefrin; lidocaine hydrochloride; linamarin; lincomycin hydrochloride; lindane; liothyronine sodium; lisinopril; lobeline hydrochloride; lomatin; lomefloxacin hydrochloride; lomustine, ccnu; loperamide hydrochloride; loratadine; losartan; lovastatin; lupinine; lysyltryptophanyl-lysine acetate; mafenide hydrochloride; maprotiline hydrochloride; marmesin; marmesin acetate; maxolon; mebendazole; mebeverine hydrochloride; mebhydrolin naphthalenesulfonate; mechlorethamine; meclizine hydrochloride; meclocycline sulfosalicylate; meclofenoxate hydrochloride; meclomen; mecysteine hydrochloride; medroxyprogesterone 17-acetate; medroxyprogesterone acetate; medrysone; mefenamic acid; mefexamide; mefloquine; mefloquine hydrochloride; megestrol acetate; melatonin; meloxicam; melphalan; melphalan; memantine hydrochloride; menadione; mepenzolate bromide; mephenesin; mephentermine sulfate; mephentoin; mepivacaine hydrochloride; merbromin; mercaptopurine; mercaptopurine; mesna; mestinon; metampicillin sodium; metaproterenol; metaraminolbitartrate; metergoline; methacholine chloride; methacycline hydrochloride; methapyrilene hydrochloride; methazolamide; methenamine; methicillin sodium; methimazole; methionyl-leucylphenylalanine acetate; methocarbamol; methoprene(s); methotrexate; methoxamine hydrochloride; methoxsalen; methoxsalen; methoxyvone; methscopolamine bromide; methylbenzethonium chloride; methyldopa; methylergonovine maleate; methylprednisolone; methylthiouracil; metolazone; metoprolol tartrate; metronidazole; metyrapone; mexitil; miconazole nitrate; micropenin; midodrine hydrochloride; mimosine; minaprine hydrochloride; minocycline hydrochloride; minoxidil; miochol; mirtazapine; mitomycin c; mitotane; mitotane; mitoxanthrone hydrochloride; mitoxantrone; mitoxantrone; mizoribine; moban; molsidomine; monensin sodium (monensin a is shown); monocrotaline; morin; moxalactam disodium; moxifloxacin hydrochloride; mupirocin; mycophenolic acid; n (g)-nitro-1-arginine; n,n-hexamethyleneamiloride; n-(2-aminoethyl)-4-chlorobenzamide (ro-16-6491); n-(3-trifluoromethylphenyl)piperazine hydrochloride (TFMPP); n-(9-fluorenylmethoxycarbonyl)-1-leucine (npc-15199); n-aminohexyl-5-chloro-1-napthalenesulfonamide hydrochloride (w-7 HCl); n-formylmethionyl-leucylphenylalanine; n-formylmethionylalanine; n-methyl (−)ephedrine; n-methyl-d-aspartic acid (nmda); nabumetone; nadide; nadolol; nafronyl oxalate; nalbuphine hydrochloride; nalidixic acid; naloxone hydrochloride; naltrexone hydrochloride; naphazoline hydrochloride; naringenin; naringin; nefopam; nelarabine; neohesperidin dihydrochalcone; neostigmine bromide; nerol; niacin; nicardipine hydrochloride; nicergoline; nicolsamide; nicotine; nicotine ditartrate; nicotinic acid; nicotinyl tartrate; nifedipine; nifenazone; niflumic acid; nigericin sodium; nilotinib; nilutamide; nimesulide; nimustine; nipecotic acid; nitrofurantoin; nitrofurazone; nitrogen mustard; nitromide; norcantharidin; nordihydroguaretic acid; norepinephrine; norethindrone; norethindrone acetate; norethynodrel; norflex; norfloxacin; norgestrel; norpace; norpramin; nortriptyline; noscapine hydrochloride; novobiocin sodium; novocain; nylidrin hydrochloride; nystatin; o-benzyl-1-serine; octopamine hydrochloride; ofloxacin; oleandomycin phosphate; olmesartan medoxomil; ondansetron; orlistat; orphenadrine citrate; osthol; ouabain; oxacillin sodium; oxaliplatin; oxcarbazepine; oxethazaine; oxidopamine hydrochloride; oxolinic acid; oxotremorine sesquifumarate; oxybendazole; oxybenzone; oxybutynin chloride; oxymetazoline hydrochloride; oxyphenbutazone; oxyphencyclimine hydrochloride; oxyquinoline; oxytetracycline; oxytetracycline hydrochloride; p-chlorophenylalanine; p-fluorophenylalanine; paclitaxel; paclitaxel; pamelor; papaverine hydrochloride; parachlorophenol; pararosaniline pamoate; pargyline hydrochloride; paromomycin sulfate; paroxetine; paroxetine hydrochloride; parthenolide; pasiniazid; pazopanib HCl; pemetrexed; penicillamine; penicillin g potassium; penicillin v; penicillin v potassium; pentamidine isethionate; pentobarbital; pentolinium tartrate; pentostatin; pentoxifylline;

pergolide mesylate; perhexyline maleate; periciazine; perillic acid (−); perindopril erbumine; perphenazine; peruvoside; peucedanin; pfizerpen; phenacemide; phenacetin; phenazopyridine hydrochloride; phenelzine; phenelzine sulfate; phenergan; phenethicillin potassium; phenindione; pheniramine maleate; phenolphthalein; phenothrin; phenoxybenzamine hydrochloride; phentolamine HCl; phentolamine hydrochloride; phenylbiguanide; phenylbutazone; phenylbutyrate sodium; phenylephrine hydrochloride; phenylmercuric acetate; phenyloin sodium; phthalylsulfathiazole; phylloquinone; physostigmine salicylate; picropodophyllotoxin; picropodophyllotoxin acetate; picrotin; picrotoxinin; pilocarpine nitrate; pimethixene maleate; pimozide; pimpinellin; pindolol; pioglitazone hydrochloride; pipemidic acid; pipenzolate bromide; piperacillin sodium; piperacillin sodium salt; piperidolate hydrochloride; piperine; pipobroman; pipobroman; piracetam; pirenperone; pirenzepine hydrochloride; piroxicam; plicamycin; podofilox; polymyxin b sulfate; pomiferin; potassium p-aminobenzoate; practolol; pralatrexate; pralidoxime mesylate; pramoxine hydrochloride; praziquantel; prazosin hydrochloride; prednisolone; prednisolone acetate; prednisone; pregnenolone; pridinol methanesulfonate; prilocalne hydrochloride; primaquine diphosphate; primidone; priscoline; pristimerin; pro-amatine; pro-banthine; proadifen hydrochloride; probenecid; probucol; procainamide hydrochloride; procaine hydrochloride; procarbazine; prochlorperazine edisylate; procyclidine hydrochloride; progesterone; proglumide; promazine hydrochloride; promethazine hydrochloride; pronestyl; pronetalol hydrochloride; propafenone hydrochloride; propantheline bromide; propiomazine maleate; propofol; propranolol hydrochloride; propylthiouracil; protoporphyrin ix; protoveratrine a; protoveratrine b; proxymetacaine; prozac; pseudoephedrine hydrochloride; pteryxin; puromycin hydrochloride; putrescine dihydrochloride; pyrantel pamoate; pyrazinamide; pyridine-2-aldoxime methochloride; pyridostigmine bromide; pyrilamine maleate; pyrimethamine; pyrithione zinc; pyrithyldione; pyrvinium pamoate; quassin; quercetin; quercitrin; quinacrine hydrochloride; quinalizarin; quinapril hydrochloride; quinidine gluconate; quinidine hydrochloride monohydrate; quinine ethyl carbonate; quinine sulfate; quinolinic acid; quipazine maleate; racephedrine hydrochloride; raloxifene HCl; ramifenazone; ramipril; ranitidine; ranitidine hydrochloride; rapamycin; rauwolscine hydrochloride; reserpine; resorcinol; resorcinol monoacetate; retinoic acid; retinyl acetate; retinyl palmitate; rhapontin; ribavirin; ribostamycin sulfate; rifabutin; rifampicin; rifampin; rifapentine; ritanserin; ritodrine hydrochloride; rofecoxib; romidepsin; ronidazole; rosolic acid; rosuvastatin; rotenone; roxarsone; roxithromycin; rutilantinone; rutoside (rutin); rythmol; s(−)-timolol maleate; saccharin; safrole; salicin; salicyl alcohol; salicylamide; salinomycin, sodium; salsoline; sanguinarine sulfate; scopolamine hydrobromide; scopoletin; selamectin; selinidin; semustine; sertraline; sildenafil; simvastatin; sisomicin sulfate; sodium beta-nicotinamide adenine dinucleotide phosphate; sodium dehydrocholate; sodium meclofenamate; sodium p-aminosalicylate; sodium salicylate; solasodine; sonazine; sorafenib; spaglumic acid; sparteine sulfate; spectinomycin dihydrochloride pentahydrate; spectinomycin hydrochloride; spermidine trihydrochloride; spiperone; spiramycin; spironolactone; stavudine; stearoylcarnitine chloride; streptomycin sulfate; streptozocin; streptozosin; strophanthidin; strychnine; succinylsulfathiazole; sulconazole nitrate; sulfabenzamide; sulfacetamide; sulfachlorpyridazine; sulfadiazine; sulfadimethoxine; sulfaguanidine; sulfamerazine; sulfameter; sulfamethazine; sulfamethizole; sulfamethoxazole; sulfamethoxypyridazine; sulfamonomethoxine; sulfanilamide; sulfanitran; sulfaphenazole; sulfapyridine; sulfaquinoxaline sodium; sulfasalazine; sulfathiazole; sulfinpyrazone; sulfisoxazole; sulindac; sulmazole; suloctidil; sulpiride; sunitinib; suprofen; suxibuzone; symmetrel; tamoxifen; tamoxifen citrate; tannic acid; tegaserod maleate; temozolomide; teniposide; teniposide; tenoxicam; terazosin; terbutaline hemisulfate; terbutaline sulfate; testosterone; testosterone propionate; tetracaine hydrochloride; tetrachloroisophthalonitrile; tetracycline; tetracycline hydrochloride; tetrahydropalmatine; tetrahydrozoline hydrochloride; tetrandrine; tetroquinone; thalidomide; thalidomide; theobromine; theophylline; thiabendazole; thiamphenicol; thiamylal sodium; thimerosal; thioctic acid; thiodiglycol; thioguanine; thioguanine; thiopental sodium; thioridazine hydrochloride; thiotepa; thiotepa; thiothixene; thiram; thonzylamine hydrochloride; tiapride hydrochloride; tilorone; timolol maleate; tinidazole; tizanidine hydrochloride; todralazine hydrochloride; tofranil; tolazamide; tolazoline hydrochloride; tolbutamide; tolfenamic acid; tolmetin sodium; tolnaftate; tolperisone hydrochloride; tolterodine hydrochloride; tomatine; topotecan HCl; torsemide; tranexamic acid; tranylcypromine sulfate; trazodone hydrochloride; tretinoin; tretinon; triacetin; triamcinolone; triamcinolone acetonide; triamcinolone diacetate; triamterene; trichlormethiazide; trichlormethine; triclosan; triethylenemelamine; trifluoperazine hydrochloride; triflupromazine hydrochloride; trifluridine; trihexyphenidyl hydrochloride; trimedlure; trimeprazine tartrate; trimethobenzamide hydrochloride; trimethoprim; trimetozine; trimipramine maleate; trioxsalen; tripelennamine citrate; triprolidine hydrochloride; trisodium ethylenediamine tetracetate; tropicamide; tryptamine; tryptophan; tuaminoheptane sulfate; tulobuterol; tyramine; tyrothricin; tyzine; uracil mustard; urapidil; urea; urecholine; urethane; uridine triphosphate trisodium; ursinic acid; ursodeoxycholic acid; ursodiol; usnic acid; valproate sodium; valproic acid; valrubicin; vancomycin hydrochloride; vandetanib; vemurafenib; verapamil hydrochloride; veratrine sulfate; vesamicol hydrochloride; vinblastine sulfate; vincamine; vincristine sulfate; vinorelbine tartrate; vistaril pamoate; vorinostat; vulpinic acid; warfarin; warfarin sodium; westcort; xanthurenic acid; xylazine; xylometazoline hydrochloride; yohimbic acid; yohimbine hydrochloride; zaprinast; zidovudine; zidovudine [azt]; zolendronic acid; zomepirac sodium; zonisamide; and zoxazolamine.

Cells

Disclosed herein, in certain embodiments, are methods of identifying a drug or nutraceutical candidate for normalizing, or partially normalizing, an optically-visible rare-disease cell phenotype in a subject in need thereof, comprising (a) contacting a plurality of cells having the optically-visible rare-disease cell phenotype with a drug or nutraceutical from a drug/nutraceutical library, (b) obtaining a magnified image of the plurality of cells following contact with the drug or nutraceutical from the drug/nutraceutical library; and (c) analyzing the magnified images to determine the response of the plurality of cells to the drug or nutraceutical from the drug/nutraceutical library. Further disclosed herein, in certain embodiments, are rare disease theranostics platforms, comprising: (a) a cell-phenotype image-enhancing instrument; (b) a drug/nutraceutical library; and (c) a computer-implemented system for analyzing a response of an optically-visible rare-disease cell phenotype to a drug or nutraceutical from the drug/nutraceutical library.

In some embodiments, a cell having the optically-visible rare-disease cell phenotype is derived from a biological fluid, e.g., blood. In some embodiments, a cell having the optically-visible rare-disease cell phenotype is derived from a biopsy (e.g., a skin biopsy, a muscle biopsy, a bone marrow biopsy, a liver biopsy, a gastrointestinal biopsy, a lung biopsy, a nervous system biopsy, a lymph node biopsy). Non-limiting examples of cells that may have an optically-visible rare-disease cell phenotype include blood cells (erythrocytes), immune cells (e.g., monocytes, macrophages, neutrophils, eosinophils, basophils, mast cells, T cells, B cells, NK cells), myocytes (e.g., skeletal muscle cells (e.g., red skeletal muscle cells or white skeletal muscle cells), myocardiocytes), fibroblasts, osteoblasts, osteocytes, adipocytes (e.g., unilocular cells, multilocular cells), hepatocytes, glial cells (e.g., astrocytes, oligodendrocytes, Schwann cells), neurons, epidermal cells (e.g., keratinocytes, melanocytes, Langerhans cells, Merkel cells).

In some embodiments, the cells are naturally-occurring cells (e.g., fibroblasts) obtained from a subject with a rare disease cell phenotype. In some embodiments, the cells are derived (e.g., differentiated) from stem cells obtained from a subject with a rare disease cell phenotype. In some embodiments, the cells are derived (e.g., differentiated) from iPS cells (induced pluripotent stem cells) produced from cells from a subject with a rare disease cell phenotype. In some embodiments, the cells are recombinant cells (e.g., they comprise a non-naturally occurring maker such as an antibiotic resistance gene or a fluorescent marker).

Production of Cells and Cell Lines

In some embodiments, the platforms and methods disclosed herein further comprise establishing a cell line comprising a plurality of cells with an optically-visible rare-disease cell phenotype. In some embodiments, the cell line comprising a plurality of cells with an optically-visible rare-disease cell phenotype is established from a stem cell line or iPS cell line obtained from an individual with an optically-visible rare disease cell phenotype. Any suitable method of establishing and maintaining cell lines may be used with the methods and platforms disclosed herein.

In some embodiments, the cell line is a differentiated cell line (e.g., a fibroblast cell line). In some embodiments, cells are isolated from a subject with a rare-disease cell phenotype. In some embodiments, the cells are maintained in culture by any suitable method using any suitable media. For example, fibroblasts may be grown in Dulbecco's Modified Eagle Medium supplemented with 10% Fetal Bovine Serum, 2 mM L-glutamine, and 0.1 mM 2-mercaptoethanol at 37° C. with 5% $CO_2$. In some embodiments, the cells are passaged until senescence (e.g., until the Hayflick limit is reached).

In some embodiments, a stem cell line or iPS cell line is used to avoid senescence of a cell line of differentiated cells with an optically-visible rare-disease cell phenotype. As used herein, "senescence" means the phenomenon by which normal cells lose the ability to divide. In differentiated cell, senescence normally occurs after about 50 cell divisions in vitro. The "Hayflick limit" refers to the maximum number of passages a cell may undergo before senescence.

As used herein, a "stem cell" is a cell that is capable of self-renewal and is potent (e.g., omnipotent, pluripotent, multipotent, oligopotent). The stem cell may be an embryonic stem cell or an adult stem cell. The stem cell may be a hematopoietic stem cell, a skeletal stem cell, a neural stem cell, or a mesenchymal stem cell.

In some embodiments, stem cells are isolated from a subject with a rare-disease cell phenotype. In some embodiments, the stem cells are maintained in culture by any suitable method using any suitable media. In some embodiments, the stem cells are maintained undifferentiated in culture by any suitable method using any suitable media. For example, the stem cells are grown on a 3D hydrogel or on plates with a "nano-patterned" surface. Where the stem cells are mesenchymal stem cells, the cells may be grown on CELLstart™ (Invitrogen) in MesenPRO RS™ Medium (Invitrogen) in order to maintain potency.

As used herein, an "iPS cell" is a pluripotent cell artificially derived from a non-pluripotent cell with an optically visible rare disease cell phenotype. The iPS cell is derived by inducing expression of specific genes that dedifferentiate the non-pluripotent cell and/or contacting the non-pluripotent cell with one or more small molecules that dedifferentiate the non-pluripotent cell.

Any suitable method is used to produce an iPS. Generally, an iPS is produced by isolating cells (e.g., fibroblasts) from a donor (e.g., an individual with a rare disease of interest), transfecting genes that induce dedifferentiation (e.g., Oct-3/4 (Pou5fl), Sox2, c-MYC, Klf4, Nanog, and/or LIN28) into the cells (e.g., by viral vectors) and/or contacting the cells with small molecules that mimic transcription factors, and harvesting and culturing the transfected cells using stem cell culture protocols.

iPS cells for use with the methods and platforms disclosed herein may have any of the following features:

Morphology: The iPS cells may have a round shape, large nucleolus and scant cytoplasm. Colonies of iPS cells may form sharp-edged, flat, tightly-packed colonies.

Growth properties: The iPS cells may be mitotically active, actively self-renewing, proliferating, and divide at a rate equal to stem cells.

Stem cell markers: The iPS cells may express SSEA-3, SSEA-4, TRA-1-60, TRA-1-81, TRA-2-49/6E, and Nanog.

Stem Cell Genes: The iPS cells may express OCT-3/4, SOX2, NANOG, GDF3, REX1, FGF4, ESG1, DPPA2, DPPA4, and hTERT.

Telomerase activity: The iPS cells may demonstrate high telomerase activity and express hTERT (human telomerase reverse transcriptase).

Pluripotency: The iPS cells may be capable of differentiation into fully differentiated tissues.

In some embodiments, the cells are recombinant cells. In some embodiments, the cells are transfected with a marker gene (e.g., an antibiotic resistance gene, or a fluorescence gene such as a gene encoding GFP) using any suitable method. For example, a fibroblast cell line is grown in Dulbecco's Modified Eagle Medium supplemented with 10% Fetal Bovine Serum, 2 mM L-glutamine, and 0.1 mM 2-mercaptoethanol at 37° C. with 5% $CO_2$ to 60% confluency. The DNA encoding the antibiotic resistance gene is precipitated in ethanol and resuspended in sterile water or TE buffer to a final concentration of 0.2-1 mg/ml. The resuspended DNA is mixed with cell growth medium and the transfection reagent (e.g., TransFast™ Reagent) to form transfection medium. The growth medium is removed from the fibroblast cell culture and the transfection medium is added to the fibroblasts cells.

Personalized Cell Lines

In some embodiments, a personalized cell line is established for a donor individual with an optically-visible rare-disease cell phenotype, wherein the personalized cell line is used to identify a drug or nutraceutical candidate for normalizing, or partially normalizing, the optically-visible rare-disease cell phenotype in that donor individual.

In some embodiments, a personalized stem cell line is established from a stem cell obtained from an individual with an optically-visible rare-disease cell phenotype. In some embodiments, a plurality of stem cells from the stem cell line is differentiated into a plurality of differentiated cells with the optically-visible rare-disease cell phenotype. In some embodiments, the differentiated cells with the optically-visible rare-disease cell phenotype are used to establish a cell line to identify a drug or nutraceutical candidate for normalizing, or partially normalizing, the optically-visible rare-disease cell phenotype in the individual with the optically-visible rare-disease cell phenotype.

In some embodiments, a personalized iPS cell line is established from a cell obtained from an individual with an optically-visible rare-disease cell phenotype. In some embodiments, the platforms and methods disclosed herein further comprise (a) dedifferentiating a cell obtained from the individual into an iPS cell (e.g., to establish a cell line), and then (b) differentiating the iPS cell into a cell with the optically-visible rare-disease cell phenotype (e.g., for use to identify a drug or nutraceutical candidate for normalizing, or partially normalizing, the optically-visible rare-disease cell phenotype in the individual).

General Cell Lines

In some embodiments, a general cell line is established from a cell obtained from a donor individual with an optically-visible rare-disease cell phenotype. In some embodiments, a general cell line is used to identify a drug or nutraceutical candidate for normalizing, or partially normalizing, the optically-visible rare-disease cell phenotype in the donor individual or any individual with the optically-visible rare-disease cell phenotype. In some embodiments, the cell line corresponds to a particular subtype (e.g., gradation) of the optically-visible rare-disease cell phenotype. For example, a general cell line may be established for an optically-visible rare-disease cell phenotype; or, a general cell line may be established for (a) a severe form of the optically-visible rare-disease cell phenotype, (b) a moderate form of the optically-visible rare-disease cell phenotype, and/or (c) an undetectable form of the optically-visible rare-disease cell phenotype.

In some embodiments, a general stem cell line is established from a stem cell obtained from a donor individual with an optically-visible rare-disease cell phenotype. In some embodiments, a plurality of stem cells from the stem cell line is differentiated into a plurality of differentiated cells with the optically-visible rare-disease cell phenotype. In some embodiments, the differentiated cells with the optically-visible rare-disease cell phenotype are used to establish a cell line to identify a drug or nutraceutical candidate for normalizing, or partially normalizing, the optically-visible rare-disease cell phenotype in the donor individual or any individual with the optically-visible rare-disease cell phenotype.

In some embodiments, a general iPS cell line is established from a cell obtained from a donor individual with an optically-visible rare-disease cell phenotype. In some embodiments, the platforms and methods disclosed herein further comprise (a) dedifferentiating a cell obtained from the donor individual into an iPS cell (e.g., to establish a cell line), and then (b) differentiating the iPS cell into a cell with the optically-visible rare-disease cell phenotype (e.g., for use to identify a drug or nutraceutical candidate for normalizing, or partially normalizing, the optically-visible rare-disease cell phenotype in the donor individual or in any individual with the optically-visible rare-disease cell phenotype).

Rare-Disease Specific Drug Libraries

Disclosed herein, in certain embodiments, are rare disease specific drug libraries identified by the methods and platforms disclosed herein. In some embodiments, a general rare disease specific drug library is identified using a cell line obtained from an individual with the rare disease cell phenotype, e.g., a general cell line. In some embodiments, the general rare disease specific drug library is screened with a personalized cell line to identify a personalized rare disease specific drug sub-library that is specific to an individual. In some embodiments, the general rare disease specific drug library is screened with a personalized cell line to optimize the dosages of the drugs in the generalized rare disease specific drug library for an individual. For example, a first individual presents with a rare disease. Cells are obtained from the individual and used to establish a rare disease general cell line. The general cell line is used to identify a general rare disease specific drug library with 6 drugs. A second individual presents with the rare disease. Cells are obtained from the individual and used to establish a rare disease personalized cell line. The general rare disease specific drug library is screened with the personalized cell line and a personalized rare disease specific drug sub-library with 4 drugs is identified.

EXAMPLES

Example 1

Laminin Binding Assay to Identify Compounds that Normalize Laminin Binding Deficiency in Fibroblasts from a Muscular Dystrophy Patient Fibroblasts obtained from a muscular dystrophy patient were seeded at 3000 cells per well in 384-well plates and treated in duplicate at 10 μm with individual compounds from the drug/nutraceutical library. After 48 hours in culture conditions, the cells were exposed to serum free media containing 0.1% BSA and 10 ug/ml laminin from Engelbreth-Holm-Swarm murine sarcoma basement membrane for a period of 2 hours. Cells were then fixed with 4% paraformaldehyde and stained with DAPI and a laminin-specific antibody, followed by a fluorescently labeled secondary antibody directed against the laminin specific antibody. The plates were then scanned using an Opera high content confocal microscopy screening system (PerkinElmer) at 20× magnification with separate fluorescent exposures, utilizing a UV light source and a 561 nm laser.

Image analysis was performed to quantify levels of laminin staining using a customized algorithm written with Acapella software (Perkin Elmer). The cytoplasm was defined using DAPI staining as a mask, and the average cytoplasmic intensity of fluorescence per cell was calculated on the basis of at least six random fields captured per well.

A compound in the drug/nutraceutical library was considered to normalize the level of fibroblast laminin binding if the compound scored at least 20% activity compared with controls. Fibroblasts from a healthy individual, or from patient cells treated with Trichostatin A at 2 uM were used as positive controls.

Trichostatin A and SAHA were identified as hits in the assay. Trichostatin A, SAHA, and Givinostat (another HDAC inhibitor in the same class as Trichostatin A and SAHA) were further tested in an eight-point dose-response assay (at a range of 20-0.02 μm, at three fold dilutions) in triplicate.

Example 2

Use of the High-Content Screen to Identify Drugs/Nutraceuticals that Normalize an Optically Visible Rare Disease Cell Phenotype Fibroblasts are obtained from a patient presenting with Rare Disease. The fibroblasts are placed in a 384-well plate for 48 hours, as described in Example 1.

Each well of the plate is then treated with a compound from a known drug or nutraceutical library. The fibroblasts are then scanned to search for changes in the optically visible rare disease cell phenotype. Positive compounds are then further tested to eliminate false positives. Positive compounds are also further tested to optimize concentrations and test for efficacious drug combinations. Positive hits are identified using a computer-based algorithm.

Compounds found to be effective for normalizing the optically visible Rare Disease phenotype are classified as Rare Disease Library 1 and administered to the patient in order to treat symptoms of the rare disease.

Example 3

Testing Fibroblasts from a Second Patient with a Rare Disease with Drugs/Nutraceuticals Previously Found to Normalize Cells from a Patient with the Same Rare Disease Rare Disease Library 1 (a "Rare Disease Specific Drug Library") is identified as in Example 2.

A second patient presents with Rare Disease. Fibroblasts are taken from the patient in order to identify a personalized rare disease specific sub-library specific to the second patient. The fibroblasts taken from the second patient are used to establish a personalized cell line and are plated in a 384-well plate, as described in Example 1.

Rare Disease Library 1 is screened against the second patient's personalized cell line. Positive hits are identified using a computer-based algorithm.

The positive hits are further tested with the personalized cell line of the second patient in order to eliminate false positives. Compounds found to be effective for normalizing the optically visible Rare Disease phenotype of the second individual are classified as Rare Disease Library 1a. Positive compounds are further tested to optimize concentrations and test for efficacious drug combinations.

Hits found to be effective for normalizing the optically visible rare disease phenotype in the personalized cell line are administered to the second patient in order to treat symptoms of the rare disease.

Example 4

Use of the High-Content Screen to Identify Drugs/Nutraceuticals that Normalize an Optically Visible Rare Disease Phenotype in Cells from a "Grey Patient"

A "grey patient" has been genotyped as carrying a gene mutation which leads to the Rare Disease, although the patient does not present with any symptoms of Rare Disease.

Cells from the "grey patient" are placed in a 384-well plate for 48 hours, as described in Example 1. Rare Disease Library 1 (a "Rare Disease Specific Drug Library") is screened against the "grey patient's" personalized cell line. Positive hits are identified using a computer-based algorithm.

The positive hits are further tested with the personalized cell line of the second patient in order to eliminate false positives. Compounds found to be effective for normalizing the optically visible Rare Disease phenotype of the second individual are classified as Rare Disease Library 1b. Positive compounds are further tested to optimize concentrations and test for efficacious drug combinations.

Hits found to be effective for normalizing the optically visible rare disease phenotype in the personalized cell line are administered to the second patient in order to treat symptoms of the rare disease.

What is claimed is:

1. A disease theranostics platform, comprising:
   a. an automated cell-phenotype image-enhancing instrument for detecting an optically-visible disease cell-phenotype which is characterized by abnormal laminin binding, or abnormal lamin A/C or lamin B binding;
   b. cells obtained or derived from a subject with the optically-visible disease cell-phenotype characterized by abnormal laminin binding, or abnormal lamin A/C or lamin B binding;
   c. a drug/nutraceutical library; and
   d. a computer-implemented system for analyzing responses of the optically-visible disease cell-phenotype of the cells obtained or derived from a subject with the optically-visible disease cell-phenotype to drugs or nutraceuticals from the drug/nutraceutical library, wherein the system comprises an algorithm for identifying drugs or nutraceuticals effective for normalizing or partially normalizing the optically-visible disease cell-phenotype.

2. The disease theranostics platform of claim 1, wherein the automated cell-phenotype image-enhancing instrument is a microscope and detects the response of the optically-visible disease cell-phenotype to a drug or nutraceutical from the drug/nutraceutical library; wherein the microscope comprises:
   a. detector for imaging the optically-visible disease phenotype;
   b. magnification optics having sufficient magnifying power to visualize one cell in a plurality of cells; and
   c. an available electronic memory for storing an image of a cell.

3. The disease theranostics platform of claim 1, wherein the cells obtained or derived from a subject with the optically-visible disease cell phenotype are differentiated from a stem cell obtained from the subject with the optically-visible disease cell-phenotype, wherein said subject has symptoms of a disease associated with the optically-visible disease cell phenotype, has limited symptoms of the disease associated with the optically-visible disease cell phenotype or is asymptomatic, and the computer-implemented system comprises an algorithm that correlates the optically-visible disease cell-phenotype with the severity of the disease associated with the optically-visible disease cell phenotype in the subject.

4. The disease theranostics platform of claim 1, wherein the drug/nutraceutical library comprises at least 500 commercially available nutraceuticals, approved therapeutic agents, or combinations thereof.

5. The disease theranostics platform of claim 1, wherein the computer-implemented system comprises an algorithm that determines degrees of response of the optically-visible disease cell-phenotype to a drug or nutraceutical in the drug/nutraceutical library; and the computer-implemented system correlates the degree of response of the optically-visible disease cell-phenotype to the drug or nutraceutical in the drug/nutraceutical library with an effect of the drug or nutraceutical on at least one symptom of a disease associated with the optically-visible disease cell phenotype in vivo.

6. The disease theranostics platform of claim 1, further comprising an assay for a biomarker that correlates with the optically-visible disease cell-phenotype, wherein the biomarker is present in blood, plasma, or cell culture medium.

7. The disease theranostics platform of claim 1, wherein the optically-visible disease cell-phenotype comprises a fluorescent tag.

8. The disease theranostics platform of claim 1, wherein the optically-visible disease cell-phenotype is cell morphology, nuclear morphology or morphology of any cytosolic organelle.

9. The disease theranostics platform of claim 1, wherein the optically-visible disease cell-phenotype is associated with a disease, wherein the disease is laminopathy, Fukuyama congenital muscular dystrophy (FCMD), congenital muscular dystrophy unrelated to FCMD, Duchenne muscular dystrophy, Becker's muscular dystrophy, distal muscular dystrophy, Emery-Dreifuss muscular dystrophy, facioscapulohumeral muscular dystrophy, Limb-girdle muscular dystrophy, myotonic muscular dystrophy, oculopharyngeal muscular dystrophy, junctional epidermolysis bullosa, or nephrotic syndrome.

10. The disease theranostics platform of claim 1, wherein the optically-visible disease cell-phenotype is associated with a rare disease, wherein the rare disease affects less than 200,000 persons in a United States population.

11. A method of identifying a drug or nutraceutical candidate for normalizing, or partially normalizing, an optically-visible disease cell phenotype which is characterized by abnormal laminin binding, or abnormal lamin A/C or lamin B binding in a subject in need thereof, comprising the steps of:
  a. contacting a plurality of cells with the optically-visible disease cell phenotype with a drug or nutraceutical from a drug/nutraceutical library;
  b. using an automated cell-phenotype image-enhancing instrument to obtain a magnified image of the plurality of cells following contact with the drug or nutraceutical from the drug/nutraceutical library, wherein the automated cell-phenotype image-enhancing instrument is configured for detecting the optically-visible disease cell phenotype characterized by abnormal laminin binding, or abnormal lamin A/C or lamin B binding; and
  c. using a computer-implemented algorithm to analyze the magnified image to determine the response of the plurality of cells to the drug or nutraceutical from the drug/nutraceutical library;

wherein a drug or nutraceutical that normalizes or partially normalizes the optically-visible disease cell phenotype is identified by the computer-implemented algorithm as a candidate for normalizing, or partially normalizing the optically-visible disease cell phenotype in the subject in need thereof.

12. The method of claim 11, wherein the subject in need thereof has symptoms of a disease associated with the optically-visible disease cell-phenotype, has limited symptoms of the disease or is asymptomatic.

13. The method of claim 11, wherein the optically visible disease cell-phenotype is cell morphology, nuclear morphology or morphology of any cytosolic organelle.

14. The method of claim 11, comprising using a microscope to obtain the magnified image of the plurality of cells.

15. The method of claim 11, further comprising assaying for a biomarker that correlates with a disease phenotype associated with the optically-visible disease cell-phenotype, wherein the biomarker is present in blood, plasma, or cell culture medium.

16. The method of claim 11, further comprising contacting the plurality of cells with a fluorescent tag to produce the optically-visible disease cell phenotype.

17. The method of claim 11, further comprising using a computer-implemented algorithm to correlate the optically-visible disease cell-phenotype with a severity of the optically-visible disease cell-phenotype in vivo.

18. The method of claim 11, wherein the optically-visible disease cell-phenotype is associated with a disease, wherein the disease is laminopathy, Fukuyama congenital muscular dystrophy(FCMD), congenital muscular dystrophy unrelated to FCMD, Duchenne muscular dystrophy, Becker's muscular dystrophy, distal muscular dystrophy, Emery-Dreifuss muscular dystrophy, facioscapulohumeral muscular dystrophy, Limb-girdle muscular dystrophy, myotonic muscular dystrophy, oculopharyngeal muscular dystrophy, junctional epidermolysis bullosa, or nephrotic syndrome.

* * * * *